(12) United States Patent
Mustakos et al.

(10) Patent No.: US 10,780,282 B2
(45) Date of Patent: Sep. 22, 2020

(54) SYSTEMS AND METHODS FOR STEERING ELECTRICAL STIMULATION OF PATIENT TISSUE AND DETERMINING STIMULATION PARAMETERS

(71) Applicant: Boston Scientific Neuromodulation Corporation, Valencia, CA (US)

(72) Inventors: Richard Mustakos, Thousand Oaks, CA (US); G. Karl Steinke, Valencia, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 160 days.

(21) Appl. No.: 15/706,004

(22) Filed: Sep. 15, 2017

(65) Prior Publication Data

US 2018/0078776 A1 Mar. 22, 2018

Related U.S. Application Data

(60) Provisional application No. 62/397,256, filed on Sep. 20, 2016.

(51) Int. Cl.
*A61N 1/372* (2006.01)
*A61N 1/36* (2006.01)
(Continued)

(52) U.S. Cl.
CPC ..... *A61N 1/37247* (2013.01); *A61N 1/36182* (2013.01); *G16H 20/30* (2018.01);
(Continued)

(58) Field of Classification Search
CPC .............. A61N 1/0534; A61N 1/36182; A61N 1/36185; A61N 1/37; A61N 1/37247
(Continued)

(56) References Cited

U.S. PATENT DOCUMENTS 3,999,555 A 12/1976 Person
4,144,889 A 3/1979 Tyers et al.
(Continued)

FOREIGN PATENT DOCUMENTS

EP 1048320 11/2000
EP 1166819 1/2002
(Continued)

OTHER PUBLICATIONS

Nowinski, W. L., et al , "Statistical analysis of 168 bilateral subthalamic nucleus implantations by means of the probabilistic functional atlas.", Neurosurgery 57(4 Suppl) (Oct. 2005),319-30.
(Continued)

*Primary Examiner* — Christopher A Flory
(74) *Attorney, Agent, or Firm* — Lowe Graham Jones PLLC; Bruce E. Black

(57) ABSTRACT

A method for determining a set of stimulation parameters for an electrical stimulation lead or steering electrical stimulation includes receiving a target geometrical parameter describing a stimulation field; receiving a first programming state; determining a first stimulation parameter for the first programming state that achieves the target geometrical parameter within at least 10% of the target geometrical parameter; and outputting set of stimulation parameters to be received by an electrical stimulation device for delivery of electrical stimulation to a patient via an electrical stimulation lead, wherein the set of stimulation parameters comprises the first stimulation parameter and represents the first programming state. In other embodiments, the target geometrical parameter is determined from either i) a first set of stimulation parameters or ii) a starting programming state and starting first stimulation parameter.

19 Claims, 9 Drawing Sheets

US 10,780,282 B2
Page 2

(51) Int. Cl.
  *G16H 40/63*  (2018.01)
  *G16H 20/30*  (2018.01)
  *A61N 1/05*  (2006.01)
  *G16H 50/50*  (2018.01)

(52) U.S. Cl.
  CPC ........... *G16H 40/63* (2018.01); *A61N 1/0534* (2013.01); *A61N 1/36064* (2013.01); *A61N 1/36067* (2013.01); *A61N 1/36082* (2013.01); *G16H 50/50* (2018.01)

(58) Field of Classification Search
  USPC ....................................................... 607/59
  See application file for complete search history.

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulman |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | DiLorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1* | 8/2003 | Woods ............... A61N 1/36071 607/46 |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,136,518 B2 | 5/2006 | Griffin et al. |
| 7,058,446 B2 | 6/2006 | Schuler et al. |

(56) References Cited

U.S. PATENT DOCUMENTS

| | | |
|---|---|---|
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,382 B2 | 3/2008 | McIntyre et al. |
| 7,388,974 B2 | 6/2008 | Yanagita |
| 7,450,997 B1 | 11/2008 | Pianca et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,000,794 B2 | 8/2011 | Lozano |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,271,094 B1 | 9/2012 | Moffitt et al. |
| 8,280,514 B2 | 10/2012 | Lozano et al. |
| 8,295,944 B2 * | 10/2012 | Howard ............... A61N 1/0534 607/116 |
| 8,326,433 B2 | 12/2012 | Blum et al. |
| 8,364,278 B2 | 1/2013 | Pianca et al. |
| 8,391,985 B2 * | 3/2013 | McDonald ........... A61N 1/0534 607/45 |
| 8,429,174 B2 | 4/2013 | Ramani et al. |
| 8,452,415 B2 | 5/2013 | Goetz et al. |
| 8,473,061 B2 | 6/2013 | Moffitt et al. |
| 8,483,237 B2 | 7/2013 | Zimmermann et al. |
| 8,543,189 B2 | 9/2013 | Paitel et al. |
| 8,571,665 B2 | 10/2013 | Moffitt et al. |
| 8,606,360 B2 | 12/2013 | Butson et al. |
| 8,620,452 B2 | 12/2013 | King et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,849,632 B2 | 9/2014 | Sparks et al. |
| 8,958,615 B2 | 2/2015 | Slum et al. |
| 9,248,272 B2 | 2/2016 | Romero |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezai |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |

(56) References Cited

U.S. PATENT DOCUMENTS

| | | |
|---|---|---|
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | Mcintyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0187222 A1 | 7/2009 | Barker |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0276021 A1 | 11/2009 | Meadows et al. |
| 2009/0281595 A1 | 11/2009 | King et al. |
| 2009/0281596 A1 | 11/2009 | King et al. |
| 2009/0287271 A1* | 11/2009 | Blum ............... A61N 1/37247 607/45 |
| 2009/0287272 A1* | 11/2009 | Kokones ............ A61N 1/37247 607/45 |
| 2009/0287273 A1* | 11/2009 | Carlton ............. A61N 1/37247 607/45 |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010488 A1* | 1/2010 | Kassab ............. A61B 18/1492 606/41 |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049031 A1* | 2/2010 | Fruland ............. A61B 18/1492 600/411 |
| 2010/0049188 A1* | 2/2010 | Nelson ............. A61B 18/1492 606/34 |
| 2010/0049192 A1* | 2/2010 | Holtz ............... A61B 18/1492 606/41 |
| 2010/0049276 A1 | 2/2010 | Blum et al. |
| 2010/0049280 A1 | 2/2010 | Goetz |
| 2010/0064249 A1 | 3/2010 | Groetken |
| 2010/0076535 A1 | 3/2010 | Pianca et al. |
| 2010/0113959 A1 | 5/2010 | Pascual-Leone et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0268298 A1 | 10/2010 | Moffitt |
| 2010/0324410 A1 | 12/2010 | Paek et al. |
| 2010/0331883 A1 | 12/2010 | Schmitz et al. |
| 2011/0004267 A1 | 1/2011 | Meadows |
| 2011/0005069 A1 | 1/2011 | Pianca |
| 2011/0040351 A1 | 2/2011 | Buston et al. |
| 2011/0066407 A1 | 3/2011 | Butson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0238129 A1 | 9/2011 | Moffitt |
| 2011/0306845 A1 | 12/2011 | Osorio |
| 2011/0306846 A1 | 12/2011 | Osorio |
| 2011/0307032 A1* | 12/2011 | Goetz ............... A61N 1/36185 607/59 |
| 2011/0313500 A1 | 12/2011 | Barker et al. |
| 2012/0016378 A1 | 1/2012 | Pianca et al. |
| 2012/0027272 A1 | 2/2012 | Akinyemi et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0078106 A1 | 3/2012 | Dentinger et al. |
| 2012/0089205 A1 | 4/2012 | Boyden et al. |

(56) References Cited

U.S. PATENT DOCUMENTS

| | | | |
|---|---|---|---|
| 2012/0101552 A1 | 4/2012 | Lazarewicz et al. | |
| 2012/0116476 A1 | 5/2012 | Kothandaraman | |
| 2012/0165898 A1 | 6/2012 | Moffitt | |
| 2012/0165901 A1 | 6/2012 | Zhu et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1 | 8/2012 | Digiore et al. | |
| 2012/0203321 A1 | 8/2012 | Moffitt et al. | |
| 2012/0207378 A1 | 8/2012 | Gupta et al. | |
| 2012/0215106 A1* | 8/2012 | Sverdlik | A61M 31/00 600/439 |
| 2012/0226138 A1 | 9/2012 | DeSalles et al. | |
| 2012/0229468 A1 | 9/2012 | Lee et al. | |
| 2012/0265262 A1 | 10/2012 | Osorio | |
| 2012/0265268 A1 | 10/2012 | Blum et al. | |
| 2012/0271376 A1* | 10/2012 | Kokones | A61N 1/37247 607/45 |
| 2012/0302912 A1 | 11/2012 | Moffitt et al. | |
| 2012/0303087 A1 | 11/2012 | Moffitt et al. | |
| 2012/0314924 A1 | 12/2012 | Carlton et al. | |
| 2012/0316615 A1 | 12/2012 | Digiore et al. | |
| 2012/0316619 A1 | 12/2012 | Goetz et al. | |
| 2012/0330622 A1 | 12/2012 | Butson et al. | |
| 2013/0039550 A1 | 2/2013 | Blum et al. | |
| 2013/0060305 A1 | 3/2013 | Bokil | |
| 2013/0105071 A1 | 5/2013 | Digiore et al. | |
| 2013/0116744 A1 | 5/2013 | Blum et al. | |
| 2013/0116748 A1 | 5/2013 | Bokil et al. | |
| 2013/0116749 A1 | 5/2013 | Carlton et al. | |
| 2013/0116929 A1 | 5/2013 | Carlton et al. | |
| 2013/0150922 A1 | 6/2013 | Butson et al. | |
| 2013/0197424 A1 | 8/2013 | Bedenbaugh | |
| 2013/0197602 A1 | 8/2013 | Pianca et al. | |
| 2013/0218156 A1* | 8/2013 | Kassab | A61B 18/1492 606/41 |
| 2013/0226261 A1* | 8/2013 | Sparks | A61N 1/37247 607/45 |
| 2013/0245719 A1* | 9/2013 | Zhu | A61N 1/37211 607/59 |
| 2013/0261684 A1 | 10/2013 | Howard | |
| 2013/0296995 A1* | 11/2013 | Mahmood | A61N 1/327 607/148 |
| 2013/0317587 A1 | 11/2013 | Barker | |
| 2013/0325091 A1 | 12/2013 | Pianca et al. | |
| 2014/0039587 A1 | 2/2014 | Romero | |
| 2014/0066999 A1 | 3/2014 | Carcieri et al. | |
| 2014/0067018 A1 | 3/2014 | Carcieri et al. | |
| 2014/0067022 A1 | 3/2014 | Carcieri et al. | |
| 2014/0088672 A1* | 3/2014 | Bedenbaugh | A61B 5/0478 607/116 |
| 2014/0122379 A1 | 5/2014 | Moffitt et al. | |
| 2014/0277284 A1 | 9/2014 | Chen et al. | |
| 2014/0296953 A1 | 10/2014 | Pianca et al. | |
| 2014/0343647 A1 | 11/2014 | Romero et al. | |
| 2014/0353001 A1 | 12/2014 | Romero et al. | |
| 2014/0358207 A1 | 12/2014 | Romero | |
| 2014/0358208 A1 | 12/2014 | Howard et al. | |
| 2014/0358209 A1 | 12/2014 | Romero et al. | |
| 2014/0358210 A1 | 12/2014 | Howard et al. | |
| 2015/0018915 A1 | 1/2015 | Leven | |
| 2015/0021817 A1 | 1/2015 | Romero et al. | |
| 2015/0045864 A1 | 2/2015 | Howard | |
| 2015/0051681 A1 | 2/2015 | Hershey | |
| 2015/0066111 A1 | 3/2015 | Blum et al. | |
| 2015/0066120 A1 | 3/2015 | Govea | |
| 2015/0134031 A1 | 5/2015 | Moffitt et al. | |
| 2015/0148869 A1* | 5/2015 | Dorval, II | A61N 1/0534 607/62 |
| 2015/0151113 A1 | 6/2015 | Govea et al. | |
| 2015/0335344 A1* | 11/2015 | Aljuri | A61B 34/10 606/169 |
| 2016/0022995 A1 | 1/2016 | Kothandaraman et al. | |
| 2016/0023008 A1 | 1/2016 | Kothandaraman | |
| 2016/0030749 A1 | 2/2016 | Carcieri et al. | |
| 2016/0096025 A1 | 4/2016 | Moffitt et al. | |
| 2016/0136429 A1 | 5/2016 | Massoumi et al. | |
| 2016/0136443 A1 | 5/2016 | Kothandaraman | |
| 2016/0206370 A1* | 7/2016 | Fruland | A61B 18/1492 |
| 2016/0256693 A1 | 9/2016 | Parramon | |
| 2016/0374710 A1* | 12/2016 | Sinelnikov | A61B 8/12 600/439 |
| 2016/0375248 A1 | 12/2016 | Carcieri et al. | |
| 2016/0375258 A1 | 12/2016 | Steinke | |
| 2017/0100593 A1 | 4/2017 | Zottola | |
| 2017/0231693 A1* | 8/2017 | Nelson | A61B 18/1492 606/41 |
| 2017/0252570 A1 | 9/2017 | Serrano Carmona et al. | |
| 2018/0263647 A1* | 9/2018 | Aljuri | A61B 18/148 |
| 2019/0069949 A1* | 3/2019 | Vrba | A61B 18/1492 |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/120823 A2 | 10/2010 |
| WO | 2011025865 | 3/2011 |
| WO | 2001/139779 A1 | 11/2011 |
| WO | 2011/159688 A2 | 12/2011 |
| WO | 2012088482 | 6/2012 |

OTHER PUBLICATIONS

Obeso, J. A., et al., "Deep-brain stimulation of the subthalamic nucleus or the pars interna of the globus paildus in Parkinson's disease.", N. Engl J Med., 345{13I. The Deep-Brain Stimulation for Parkinson's Disease Study Group, (Sep. 27, 2001 ),956-63.

Butson et al.. "Current Steering to control the volume of tissue activated during deep brain stimulation," vol. 1, No. 1, Dec. 3, 2007, pp. 7-15.

Patrick, S. K., et al,. "Quantification of the UPDRS rigidity scale", IEEE Transactions on Neural Systems and Rehabilitation Engineering, [see also IEEE Trans. on Rehabilitation Engineering 9(1). (2001),31-41.

Phillips, M. D., et al., "Parkinson disease: pattern of functional MR imaging activation during deep brain stimulation of subthalamic nucleus—initial experience", Radiology 239(1). (Apr. 2006),209-16.

Ericsson, A. et al., "Construction of a patient-specific atlas of the brain: Application to normal aging," Biomedical Imaging: From Nano to Macro, ISBI 2008, 5th International Symposium, May 14, 2008, pp. 480-483.

Kalkai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010 IEEE International Symposium, Apr. 14, 2010, pp. 1321-1324.

(56) References Cited

OTHER PUBLICATIONS

Olivier Commowick et al., "Using Frankenstein's Creature Pradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images,"NeuroImage, Academic Press, vol. 49, No. 3, Feb. 1, 2010, pp. 2352-2365.

McIntyre, C. C., et al., "How does deep brain stimulation work? Present understanding and future questions.", J Clin Neurophysiol. 21(1 ). (Jan.-Feb. 2004 ), 40-50.

Sanchez Castro et al., "A cross validation study of deep brain stimulation targeting: From experts to Atlas-Based, Segmentation-Based and Automatic Regristration Algorithms," IEEE Transactions on Medical Imaging, vol. 25, No. 11, Nov. 1, 2006, pp. 1440-1450.

Plaha, P. , et al., "Stimulation of the caudal zona incerta is superior to stimulation of subthalamic nucleus in improving contralateral parkinsonism.", Brain 129{Pt 7) (Jul. 2006), 1732-4 7.

Rattay, F, "Analysis of models for external stimulation of axons", IEEE Trans. Biomed. Eng. vol. 33 (1986),974-977.

Rattay, F., "Analysis of the electrical excitation of CNS neurons", IEEE Transactions on Biomedical Engineering 45 (6). (Jun. 1998),766-772.

Rose, T. L., et al., "Electrical stimulation with Pt electrodes. VII. Electrochemically safe charge injection limits with 0.2 ms pulses [neuronal application]", IEEE Transactions on Biomedical Engineering, 37(11 ), (Nov. 1990), 1118-1120.

Rubinstein, J. T.. et al., "Signal coding in cochlear implants: exploiting stochastic effects of electrical stimulation", Ann Otol Rhinol Laryngol Suppl.. 191, (Sep. 2003). 14-9.

Schwan, H.P., et al., "The conductivity of living tissues.", Ann NY Aced Sci., 65(6). (AUQ., 1957),1007-13.

Taylor, R. S., et al,, "Spinal cord stimulation for chronic back and leg pain and failed back surgery syndrome: a systematic review and analysis of prognostic factors", Spine 30(1 ). (Jan. 1, 2005), 152-60.

Siegel, Ralph M. et al., "Spatiotemporal dynamics of the functional architecture for gain fields in inferior parietal lobule of behaving monkey," Cerebral Cortex, New York, NY, vol, 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

Geddes, L. A., et al., "The specific resistance of biological material—a compendium of data for the biomedical engineer and physiologist.", Med Biol Ena. 5(3). (May, 1967).271-93.

Gimsa, J., et al., "Choosing electrodes for deep brain stimulation experiments—electrochemical considerations.", J Neurosci Methods, 142(2). (Mar. 30, 2005),251-65.

Vidailhet, M. , et al., "Bilateral deep-brain stimulation of the globus pallidus in primary generalized dystonia", N Engl J Med. 352(5) (Feb. 3, 2005),459-67.

Izad. Oliver, "Computationally Efficient Method in Predicating Axonal Excitation," Dissertation for Master Degree, Department of Biomedical Engineering, Case Western Reserve University, May 2009.

Jaccard. Paul, "Elude comparative de la distribution florale dans une portion odes Aples et des Jura," Bulletin de la Societe Vaudoise des Sciences Naturelles (1901), 37:547-579.

Dice, Lee R., "Measures of the Amount of Ecologic Association Between Species," Ecology 26(3) (1945): 297-302. doi: 10.2307/1932409, http://jstor.org/stable/1932409.

Rand, WM., "Objective criteria for the evaluation of clustering methods," Journal of the American Statistical Association (American Statistical Association) 66 (336) (1971 ): 846-850, doi: 10.2307/2284239, http://jstor.org/stable/2284239.

Hubert, Lawrence et al., "Comparing partitions," Journal of Classification 2(1) (1985): 193-218, doi:10.1007/BF01908075.

Cover, T.M. et al., "Elements of information theory," (1991) John Wiley & Sons, New York, NY.

Meila, Marina, "Comparing Clusterings by the Variation of Information," 173-187 Learning Theory and Kernel Machines (2003): 173-187.

Viola, P.. et al., "Alignment by maximization of mutual information", International Journal of Com outer Vision 24(2). ( 1997), 137-154.

Butson et al. "StimExplorer: Deep Brain Stimulation Parameter Selection Software System," Acta Neurochirugica, Jan. 1, 2007, vol. 97, No. 2, pp. 569-574.

Butson et al. "Role of Electrode Design on the Volume of Tissue Activated During Deep Brain Stimulation," Journal of Neural Engineering; Mar. 1, 2006; vol. 3, No. 1, pp. 1-8.

Volkmann et al., Indroduction to the Programming of Deep Brain Stimulators, Movement Disorders, vol. 17, Suppl. 3, pp. S181-S187 (2002).

Miocinovic et al. "Cicerone: Stereotactic Neurophysiological Recording and Deep Brain Stimulation Electrode Placement Software System," Acta Neurochirurgica Suppl., Jan. 2007, vol. 97, No. 2, pp. 561-567.

Schmidt et al. "Sketching and Composing Widgets for 3D Manipulation," Eurographics, Apr. 2008, vol. 27, No, 2, pp. 301-310.

Volkmann, J. , et al "Basic algorithms for the programming of deep brain stimulation in Parkinson's disease", Mov Disord., 21 Suppl 14. (Jun. 2006),S284-9.

Walter, B. L., et al., "Surgical treatment for Parkinson's disease", Lancet Neural. 3(12). (Dec. 2004),719-28.

Wei, X. F., et al., "Current density distributions, field distributions and impedance analysis of segmented deep brain stimulation electrodes", J Neural Eng .. 2(4). (Dec. 2005), 139-47.

Zonenshayn, M. , et al., "Location of the active contact within the subthalamic nucleus (STN) in the treatment of idiopathic Parkinson's disease.", Surg Neurol., 62(3) (Sep. 2004),216-25.

Da Silva et al (A primer on tensor imaging of anatomical substructures, Neurosurg Focus 15 (1): p. 1-4, Article 4, 2003.).

Micheli-Tzanakou, E., et al., "Computational Intelligence for target assesment in Parkinson's disease", Proceeding of SPIE vol. 4479. Applications and Science of Neural Networks, Fuzzy Systems, and Evolutionary Computation IV,(2001),54-69.

Grill, W. M., "Stimulus waveforms for selective neural stimulation", IEEE Engineering in Medicine and Biology Magazine, 14(4), (Jul.-Aug. 1995), 375-385.

Miocinovic, S., et al., "Sensitivity of temporal excitation properties to the neuronal element activated by extracellular stimulation", J Neurosci Methods. 132(1). (Jan. 15, 2004), 91-9.

Hunka, K. et al., Nursing Time to Program and Assess Deep Brain Stimulators in Movement Disorder Patients, J. Neursci Nurs., 37: 204-10 (Aug. 2005).

Moss, J. , et al., "Electron microscopy of tissue adherent to explanted electrodes in dystonia and Parkinson's disease", Brain, 127{Pt 12), (Dec. 2004),2755-63.

Montgomery, E. B., et al., "Mechanisms of deep brain stimulation and future technical developments.", Neurol Res. 22(3). (Apr. 2000),259-66.

Merrill, D. R., et al., "Electrical stimulation of excitable tissue: design of efficacious and safe protocols", J Neurosci Methods. 141(2), (Feb. 15, 2005), 171-98.

Fisekovic et al., "New Controller for Functional Electrical Stimulation Systems", Med. Eng. Phys. 2001; 23:391-399.

Zhang, Y., et al., "Atlas-guided tract reconstruction for automated and comprehensive examination of the white matter anatomy," Neuroimage 52(4) (2010), pp. 1289-1301.

""BioPSE" The Biomedical Problem Solving Environment", htt12://www.sci.utah.edu/cibc/software/index.html, MCRR Center for Integrative Biomedical Computing,(2004).

Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003),1-13.

Carnevale, N. T. et al., "The Neuron Book," Cambridge, UK: Cambridge University Press (2006), 480 pages.

Chaturvedi: "Development of Accurate Computational Models for Patient-Specific Deep Brain Stimulation," Electronic Thesis or Dissertation, Jan. 2012, 162 pages.

(56) References Cited

OTHER PUBLICATIONS

Chaturvedi, A. et al.: "Patient-specific models of deep brain stimulation: Influence of field model complexity on neural activation predictions."Brain Stimulation, Elsevier, Amsterdam, NL, vol. 3, No. Apr. 2, 2010, pp. 65-77.
Frankemolle, et al., "Reversing cognitive-motor impairments in Parkinson's disease patients using a computational modeling approach to deep brain stimulation programming," Brian 133 (2010); pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds,"IEEE Transactions on Biomedical Engineering, vol. 39, No. 12 (Dec. 1992), pp. 1244-1254.
Wesselink; et al., "Analysis of Current Density and Related Parameters in Spinal Cord Stimulation," IEEE Transactions on Rehabilitation Engineering, vol. 6, No. 2 Jun. 1998, pp. 200-207.
Andrews, R. J., "Neuroprotection trek—the next generation: neuromodulation II. Applications—epilepsy, nerve regeneration, neurotrophins.", Ann NY Acad Sci. 993 (May, 2003), 14-24.
Astrom, M. , et al., "The effect of cystic cavities on deep brain stimulation in the basal ganglia: a simulation-based study", J Neural Eng., 3(2), (Jun. 2006).132-8.
Bazin et al., "Free Software Tools for Atlas-based Volumetric Neuroimage Analysis", Proc. SPIE 5747, Medical Imaging 2005: Image Processing, 1824 May 5, 2005.
Back, C. , et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.
Brown, J. " Motor Cortex Stimulation," Neurosurgical Focus ( Sep. 15, 2001) 11(3):E5.
Budai et al., "Endogenous Opiod Peptides Acting at m-Opioid Receptors in the Dorsal Horn Contribute to Midbrain Modulation of Spinal Nociceptive Neurons," Journal of Neurophysiology (1998) 79(2): 677-687.
Casselin, F. "Opiod and anit-opiod peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C. , et al., "Modeling extracellular field potentials and the frequency-filtering properties of extracellular space", Biophys J .. 86(3). (Mar. 2004),1829-42.
Benabid, A. L., et al., "Future prospects of brain stimulation", Nuerol Res.;22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd IEEE EMBS, (Mar. 16-19, 2005), 196-197.
Mcintyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006 EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.
Butson, C. R., et al., "Deep brainstirnulation interactive visualization system", Society for Neuroscience Volume 898.7 (2005),.
Hodaie, M., et al., "Chronic anterior thalamus stimulation for intractable epilepsy," Epilepsia, 43(6) (Jun. 2002), pp. 603-608.
Hoekema, R., et at, "Muitigrid solution of the potential field in modeling electrical nerve stimulation," Comput Biomed Res., 31(5) (Oct. 1998), pp. 348-362.
Holsheimer, J., et al.. "Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001), pp. 429-434.
Jones, DK. et al., "Optimal strategies for measuring diffusion in anisotropic systems by magnetic resonance imaging," Magn. Reson. Med., 42(3) (Sep. 1999), pp. 515-525.
Krack, P., et al., "Postoperative manaaement of subthalamic nucleus stimulation for Parkinson's disease," Mov. Disord., vol. 17(suppl 3) (2002), pp. 188-197.
Le Bihan, D., et al., "Diffusion tensor imaging: concepts and applications," J Magn Reson Imaging, 13(4) (Apr. 2001), pp. 534-546.
Lee. D. C., et al., "Extracellular electrical stimulation of central neurons: quantitative studies," In: Handbook of neuroprosthetic methods, WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10(3 Suppl 1) (Aug. 1997), pp. 231-237.
Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mcintyre, C. C., et al., "Extracellular stimulation of central neurons: influence of stimulus waveform and frequency on neuronal output,"J. Nuerophysiol., 88(4), (Oct. 2002), pp. 1592-1604.
Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.
Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.
Mcintyre, C. C., et al., "Model-based design of stimulus trains for selective microstimulation of targeted neuronal populations,"Proceedings of the 23rd Annual International Conference of the IEEE Engineering in Medicine and Biology Society, vol. 1 (2001), pp. 806-809.
Mcintyre, C. C., et al., Model-based design of stimulus waveform for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.
Mcintyre, Cameron C., et al., "Modeling the excitability of mammalian nerve fibers: influence of aflerpotentials on the recovery cycle," J Neurophysiol, 87(2) (Feb. 2002), pp. 995-1006.
Mcintyre, Cameron C., et al., "Selective microstimulation of central nervous system nuerons," Annals of biomedical engineering, 28(3) (Mar. 2000), pp. 219-233.
Mcintyre, C. C., et al., "Sensitivity analysis of a model of mammalian nueral membrane," Biol Cybern., 79(1) (Jul. 1998), pp. 29-37.

(56) References Cited

OTHER PUBLICATIONS

Mcintyre, Cameron C., et al., "Uncovering the mechanism(s) of action of deep brain stimulation: activation, inhibition, or both," Clin Neurophysiol, 115(6) (Jun. 2004), pp. 1239-1248.
Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.
Mouine et al. "Multi-Strategy and Multi-Algorithm Cochlear Prostheses", Biomed. Sci. Instrument, 2000; 36:233-238.
Mcintyre, Cameron C., et al., "Electric Field and Stimulating Influence generated by Deep Brain Stimulation of the Subthalamic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
Micheli-Tzanakou, E. , et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.
Miocinovic. S., et al., "Computational analysis of subthalamic nucleus and lenticular fasciculus activation during therapeutic deep brain stimulation," J Neuraphysiol 96(3) (Sep. 2006), pp. 1569-1580.
Miranda, P. C,, et al "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C,, et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.
Moffitt, MA., et al., "Prediction of myelinated nerve fiber stimulation thresholds: limitations of linear models," IEEE Transactions on Biomedical Engineering, 51 (2) (2003), pp. 229-236.
Moro, E, et al., "The impact on Parkinson's disease of electrical parameter settings in STN stimulation," Neurology, 59 (5) (Sep. 10, 2002), pp. 706-713.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003). pp. 786-790.
Pierpaoli, C., et al., "Toward a quantitative assessment of diffusion anisotropy,"Magn Reson Med., 36(6) (Dec. 1996), pp. 893-906.
Plonsey, R., et al., "Considerations of quasi-stationarity in electrophysiological systems," Bull Math Biophys., 29(4) (Dec. 1967), pp. 657-664.
Ranck, J B.; "Specific impedance of rabbit cerebral cortex," Exp. Neurol., vol. 7 (Feb. 1963), pp. 144-152.
Ranck, J B., et al,, "The Specific impedance of the dorsal columns of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975), pp. 417-440.

Rattay, F., et al., "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Inftuence of the three-dimensional cochlear structure on neural excitability," Hear Res., 153(1-2) (Mar. 2001), pp. 64-79.
Rattay, F. "Arrival at Functional Electrostimulation by modelling of fiber excitation," Proceedings of the Ninth annual Conference of the IEEE Engineering in Medicine and Biology Society (1987), pp. 1459-1460.
Rattay; F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.
Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.
Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.
Sances, A., et al., "In Electroanesthesia: Biomedical and Biophysical Studies," A Sances and SJ Larson, Eds., Academic Press, NY (1975), pp. 114-124.
SI. Jean, P., et al., "Automated atlas integration and interactive three-dimensional visualization tools for planning and guidance functional neurosurgery," IEEE Transactions on Medical Imaging, 17(5) (1998), pp. 672-680.
Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.
Sterio, D., et al., "Neurophysiological refinement of subthalamic nucleus targeting," Neurosurgery, 50(1) (Jan. 2002), pp. 58-69.
Struijk, J, J., et al., "Excitation of dorsal root fibers in spinal cord stimulation: a theoretical study," IEEE Transactions on Biomedical Engineering, 40(7) (Jul. 1993), pp. 632-639.
Struijk, J J., et al., "Recruitment of dorsal column fibers in spinal cord stimulation: influence of collateral branching," IEEE Transactions on Biomedical Engineering, 39(9) (Sep. 1992), pp. 903-912.
Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.
Tarler; M., et al., "Comparison between monopolar and tripolar configurations in chronically implanted nerve cuff electrodes," IEEE 17th Annual Conference Engineering in Medicine and Biology Society, vol. 2 (1995), pp. 1093-109.
Testerrnan, Roy L., "Coritical response to callosal stimulation: A model for determining safe and efficient stimulus parameters," Annals of Biomedical Engineering, 6(4) (1978), pp. 438-452.
Tuch, D.S.. et al., "Conductivity mapping of biological tissue using diffusion MRI," Ann NY Acad Sci., 888 (Oct. 30, 1999), pp. 314-316.
Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al., "Selective control of muscle activation with a multipolar nerve cuff electrode,"Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. 3) (2002), pp. 69-72.
Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.

(56) References Cited

OTHER PUBLICATIONS

Wakana, S., et al., "Fiber tract-based atlas of human white matter anatomy," Radiology 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystonic conditions: a prospective audit," Mov. Disord., vol. 18, (2003), pp. 436-442.
Zonenshayn, M., et al., "Comparison of anatomic and neurophysiological methods for subthalamic nucleus targeting,"Neurosurgery, 47(2) (Aug. 2000), pp. 282-294.
Voghell et al., "Progammable Current Source Dedicated to Implantable Microstimulators"ICM '98 Proceedings of the Tenth International Conference. pp. 67-70.
Butson, Christopher R., et al., "Patient-specific analysis of the volume of tissue activated during deep brain stimulation", NeuroImage. vol. 34. (2007)661-670.
Adler DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
Alo, K. M., et al., "New trends in neuromodulation for the management of neuropathic pain," Neurosurgery, 50(4), (Apr. 2002), pp. 690-703, discussion pp. 703-704.
Ashby, P., et al,, "Neurophysiological effects of stimulation through electrodes in the human subthalamic nucleus," Brain, 122 (P1 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Oct. 2002), pp. 969-983.
Bammer, R, et al., "Diffusion tensor imaging using single-shot SENSE-EPI", Magn Reson Med., 48(1 ), (Jul. 2002), pp. 128-136.
Basser, P. J., et al., "MR diffusion tensor spectroscopy and imaging," Biophys J., 66(1 ), (Jan. 1994), pp. 259-267.
Basser, P J., et al., "New currents in electrical stimulation of excitable tissues," Annu Rev Biomed Eng., 2, (2000), pp. 377-397.
Bensbid, AL., et al., "Chronic electrical stimulation of the ventralis intermedius nucleus of the thalamus as a treatment of movement disorders," J. Neurosurg., 84(2), (Feb. 1996), pp. 203-214.
Benabid, AL., et al., "Combined (lhalamotoy and stimulation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Butson, C. R., et al., "Predicting the effects of deep brain stimulation with different tensor based electric field models," Medical Image Computing and Computer-Assisted Intervention—Mic Cal 2006, Lecture Notes in Computer Science (LNCS), vol. 4191, pp. 429-437, LNCS, Springer, Berlin, DE.
Christensen, Gary E., et al., "Volumetric transformation of brain anatomy," IEEE Transactions on Medical Imaging, 16 (6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalized dystonia by stimulation of the internal globus pallidus," Lancet, 355 (9222), (Jun. 24, 2000), pp. 2220-2221.

Dasilva, A.F. M., et al., "A Primer Diffusion Tensor Imaging of Anatomical Substructuresm," Neurosurg. Focus; 15(1) (Jul. 2003), pp. 1-4.
Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.
Finnis, K. W., et al., "3-D functional atalas of subcortical structures for image guided stereotactic neurosurgery," Neuroimage, vol. 9, No. 6, Iss. 2 (1999), p. S206.
Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes In Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes In Computer Science: vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.
Finnis, Kirk W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation and neuropsychological outcome in for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep, 1995), pp. 272-282.
Goodall, E. V., et al., "Position-selective activation of peripheral nerve fibers with a cuff electrode," IEEE Transactions Biomedical Engineering, 43(8) (Aug. 1996), pp. 851-856.
Goodall, E. V., "Simulation of activation and propagation delay during tripolar neural stimulation," Proceedings of the 15th Annual international Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual Society International Conference of the IEEE Engineering in Medicine and Biology, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.

(56) References Cited

OTHER PUBLICATIONS

Grill, W. M., et al., "Quantification of recruitment properties of multiple contact cuff electrodes," IEEE Transactions on Rehabilitation Engineering. [see also IEEE Trans. on Neural Systems and Rehabilitation], 4(2) (Jun. 1996), pp. 49-62.

Grill, W. K. "Spatially selective activation of peripheral nerve for neuroprosthetic applications," Ph.D. Case Western Reserve University, (1995), pp. 245 pages.

Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.

Grill, W. M., "Stimulus waveforms for neural stimulation," IEEE Engineering in Medicine and Biology Magazine, 14(4) (Jul.-Aug. 1995), pp. 375-385.

Grill, W. M., et al., "Temporal stability of nerve cuff electrode recruitment properties," IEEE 17th Annual Conference Engineering in Medicine and Biology Society, vol. 2 (1995), pp. 1089-1090.

Gross, Re., et al., "Advances in neurostimulation for movement disorders," Neurol Res., 22(3) (Apr. 2000), pp. 247-258.

Guridi et al., "The subthalamic nucleus, hemiballismus and Parkinson's disease: reappraisal of a neurological dogma," Brain, vol. 124, 2001, pp. 5-19.

Haberler, C, et al., "No tissue damage by chronic deep brain stimulation in Parkinson's disease," Ann Neurol,, 48(3) (Sep. 2000), pp. 372-376.

Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.

Hanekom, "Modelling encapsulation tissue around cochlear implant electrodes," Med. Biol. Eng. Comput. vol. 43 (2005), pp, 47-55.

Haueisen, J , et al., "The influence of brain tissue anisotropy on human EEG and MEG," Neuroimage, 15(1) (Jan. 2002), pp. 159-166.

D'Haese et al., Medical Image Computing and Computer-Assisted Intervention—MICCAI 2005 Lecture Notes in Computer Science, 2005, vol. 3750, 2005, 427-434.

Rohde et al. IEEE Transactions on Medical Imaging, vol. 22 No. 11, 2003 p. 1470-1479.

Dawant et al., Biomedical Image Registration. Lecture Notes in Computer Science, 2003, vol. 2717, 2003, 142-150.

Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.

Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.

Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.

Andrade-Souza, "Comparison of Three Methods of Targeting the Subthalamic Nucleus for Chronic Stimulation in Parkinson's Disease", Neurosurgery, 56:360-368, Apr. 2005.

Anheim et al., "Improvement in Parkinson Disease by Subthalamic Nucleus Stimulation Based on Electrode Placement", Arch Neural., 65:612-616, May 2008.

Butson et al., "Tissue and Electrode Capactiance Reduce Neural Activation Volumes During Deep Brain Stimulation", Clinical Neurophysiology, 116:2490-2500, Oct. 2005.

Butson et al., "Sources and Effects of Electrode Impedance During Deep Brain Stimulation", Clinical Neurophysiology, 117:44 7-454, Dec. 2005.

D'Haese et al., "Computer-Aided Placement of Deep Brain Stimulators: From Planning to Intraoperative Guidance", 24:1469-1478, Nov. 2005.

Gross et al., "Electrophysiological Mapping for the Implantation of Deep Brain Stimulators for Parkinson's Disease and Tremor", Movement Disorders, 21 :S259-S283, Jun. 2006.

Halpern et al., "Brain Shift During Deep Brain Stimulation Surgery for Parkinson's Disease", Stereotact Funct. Neurosurg., 86:37-43, published online Sep. 2007.

Herzog et al., "Most Effective Stimulation Site in Subthalamic Deep Brain Stimulation for Parkinson's Disease", Movement Disorders, 19:1050-1099, published on line Mar. 2004.

Jeon et al., A Feasibility Study of Optical Coherence Tomography for Guiding Deep Brain Probes, Journal of Neuroscience Methods, 154:96-101, Jun. 2006.

Khan et al "Assessment of Brain Shift Related to Deep Brain Stimulation Surgery", Sterreotact Funct. Neurosurge., 86:44-53, published online Sep. 2007.

Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.

Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.

Machado et al., "Deep Brain Stimulation For Parkinson's Disease: Surgical Technique and Perioperative Management", Movement Disorders, 21 :S247-S258, Jun. 2006.

Maks et al., "Deep Brain Stimulation Activation Volume and Their Association with Neurophysiological Mapping and Therapeutic Outcomes", Downloaded from jnmp.bmj.com pp. 1-21, published online Apr. 2008.

Moran et al., "Real-Time Refinment of Subthalamic Nucleous Targeting Using Bayesian Decision-Making on the Root Mean Square Measure", Movement Disorders, 21: 1425-1431. published online Jun. 2006.

Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.

Winkler et al., The First Evaluation of Brain Shift During Functional Neurosurgery by Deformation Field Analysis, J. Neural. Neurosurg. Psychiatry, 76:1161-1163, Aug. 2005.

Yelnik et al., "A Three-Dimensional, Histological and Deformable Atlas of the Human Basal J Ganglia. I. Atlas Construction Based on lmmunohistochemical and MRI Data", NeuroImage, 34:618,-638,Jan. 2007.

Ward, H. E., et al., "Update on deep brain stimulation for neuropsychiatric disorders," Neurobiol Dis 38 (3) (2010), pp. 346-353.

Alberts et al. "Bilateral subthalamic stimulation impairs cognitive-motor performance in Parkinson's disease patients." Brain (2008), 131, 3348-3360, Abstract.

Butson, Christopher R., et al., "Sources and effects of electrode impedance during deep brain stimulation", Clinical Neurophysiology. vol. 117.(2006),447-454.

An, et al., "Prefrontal cortical projections to longitudinal columns in the midbrain periaqueductal gray in macaque monkeys," J Comp Neural 401 (4) (1998), pp. 455-479.

Butson, C. R., et al., "Tissue and electrode capacitance reduce neural activation volumes during deep brain stimulation," Clinical Neurophysiology, vol. 116 (2005), pp. 2490-2500.

Carmichael, S. T., et al., "Connectional networks within the orbital and medial prefrontal cortex of macaque monkeys," J Comp Neural 371 (2) (1996), pp. 179-207.

Croxson, et al., "Quantitative investigation of connections of the prefontal cortex in the human and macaque using probabilistic diffusion tractography," J Neurosci 25 (39) (2005), pp. 8854-8866.

Frankemolle, et al., "Reversing cognitive-motor impairments in Parkinson's disease patients using a computational modelling approach to deep brain stimulation programming," Brain 133 (2010), pp. 746-761.

Freedman, et al., "Subcortical projections of area 25 (subgenual cortex) of the macaque monkey," J Comp Neurol 421 (2) (2000), pp. 172-188.

(56) References Cited

OTHER PUBLICATIONS

Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg, et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with cortical connections, providing a substrate for incentive-based learning," J Neurosci 26 (32) (2006), pp. 8368-8376.
Haber, et al,, "Cognitive and limbic circuits that are affected by deep brain stimulation", Front Biosci 14 (2009), pp. 1823-1834.
Hines, M. L., et al., "The NEURON simulation enviroment," Neural Comput., 9(6) (Aug. 15, 1997), pp. 1179-1209.
Hua, et al.. "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp, 461-467.
Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Funel. Neurosurg. 87(2009), pp, 229-240.
Machado. et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression." Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp, 471-481.
McIntyre,C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neural 216 (i) (2009),pp. 166-176.
Nuttin, et al.. "Electrical stimulation in anterior limbs of internal capsules in patients with obsessive-compulsive disorder," Lancet 354 (9189) (1999), p. 1526.
Saxena, et al.. "Cerebral glucose metabolism in obsessive-compulsive hoarding, " Am J Psychiatry. 161 (6) (2004), pp. 1038-1048.

Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001; 23:53-60.
Mcintyre, Cameron , et al., "Finite element analysis of the current-density and electric field generated by metal microelectrodes", Ann Biomed Eng . 29(3), (2001 ),227-235.
Foster, K. R., et al., "Dielectric properties of tissues and biological materials: a critical review.", Grit Rev Biomed Ena. 17(1 ). {1989),25-104.
Limousin, P., et al., "Electrical stimulation of the subthalamic nucleus in advanced Parkinson's disease," N Engl J Med .. 339(16), (Oct. 15, 1998), 1105-11.
Kitagavva, M., et al., "Two-year follow-up of chronic stimulation of the posterior subthalamic white matter for tremor-dominant Parkinson's disease.", Neurosurgery. 56(2). (Feb. 2005),281-9.
Johnson, M. D., et al., "Repeated voltage biasing improves unit recordings by reducing resistive tissue impedances", and Rehabilitation Engineering, [see also IEEE Trans. on Rehabilitation Engineering (2005), 160-165.
Holsheimer, J. , et al.. "Chronaxie calculated from current-duration and voltage-duration data", J Neurosci Methods. 97(1). (Apr. 1, 2000),45-50.
Hines, M. L., et al., "The NEURON simulation environment", Neural Comput. 9(6). (Aug. 15, 1997), 1179-209.
Herzog, J., et al., "Most effective stimulation site in subthalamic deep brain stimulation for Parkinson's disease", Mov Disord. 19(9). (Sep. 2004),1050-4.
Hershey, T., et al., "Cortical and subcortical blood flow effects of subthalamic nucleus stimulation in PD,"; Neurology 61(6). (Sep. 23, 2003),816-21.
Hemm, S. , et al., "Evolution of Brain Impedance in Dystonic Patients Treated by GPi Electrical Simulation", Neuromodulation 7(2) (Apr. 2004),67-75.
Hemm, S., et al., "Deep brain stimulation in movement disorders: stereotactic coregistration of two-dimensional electrical field modeling and magnetic resonance imaging.", J Neurosurg. 103(6): (Dec. 2005),949-55.
Haueisen, J, et al., "The influence of brain tissue anisotropy on human EEG and MEG", Neuroimage 15(1) (Jan. 2002),159-166.
Haslinger, B., et al., "Frequency-correlated decreases of motor cortex activity associated with subthalamic nucleus stimulation in Parkinson's disease.", Neuroimage 28(3). (Nov. 15, 2005),598-606.
Hashimoto, T. , et al., "Stimulation of the subthalamic nucleus changes the firing pattern of pallidal nuerons", J Neurosci. 23(5), (Mar. 1, 2003),1916-23.
Hardman. C. D., et al., "Comparison of the basal ganglia in rats, marmosets, macaques, baboons, and humans: Volume and neuronal number for the output, internal relay, and striatel modulating nuclei", J Comp Neurol., 445(3). (Apr. 8, 2002),238-55.
McNaughtan et al., "Electrochemical Issues in Impedance Tomography", 1st World Congress on Industrial Process Tomography, Buxton, Greater Manchester. Apr. 14-17, 1999.
Grill, WM., et al., "Electrical properties of implant encapsulation tissue", Ann Biomed Eng. vol. 22. (1994),23-33.
Grill, W. M., et al,, "Deep brain stimulation creates an informational lesion of the stimulated nucleus", Neuroreport. 15I7t (May 19, 2004 ), 1137-40.
Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015; 21(4):378-82.

\* cited by examiner

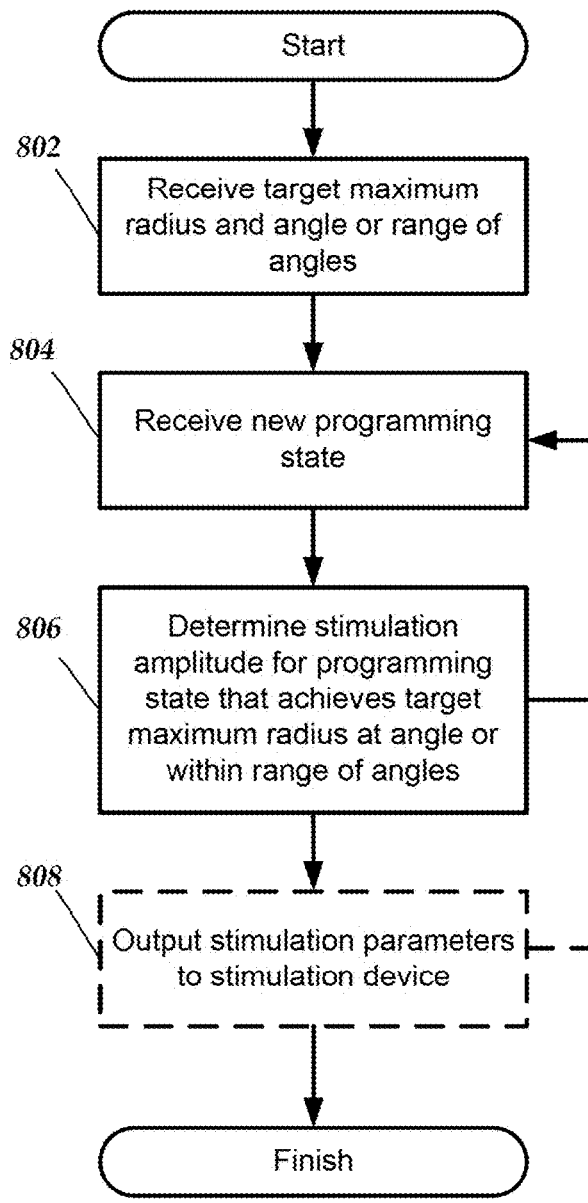
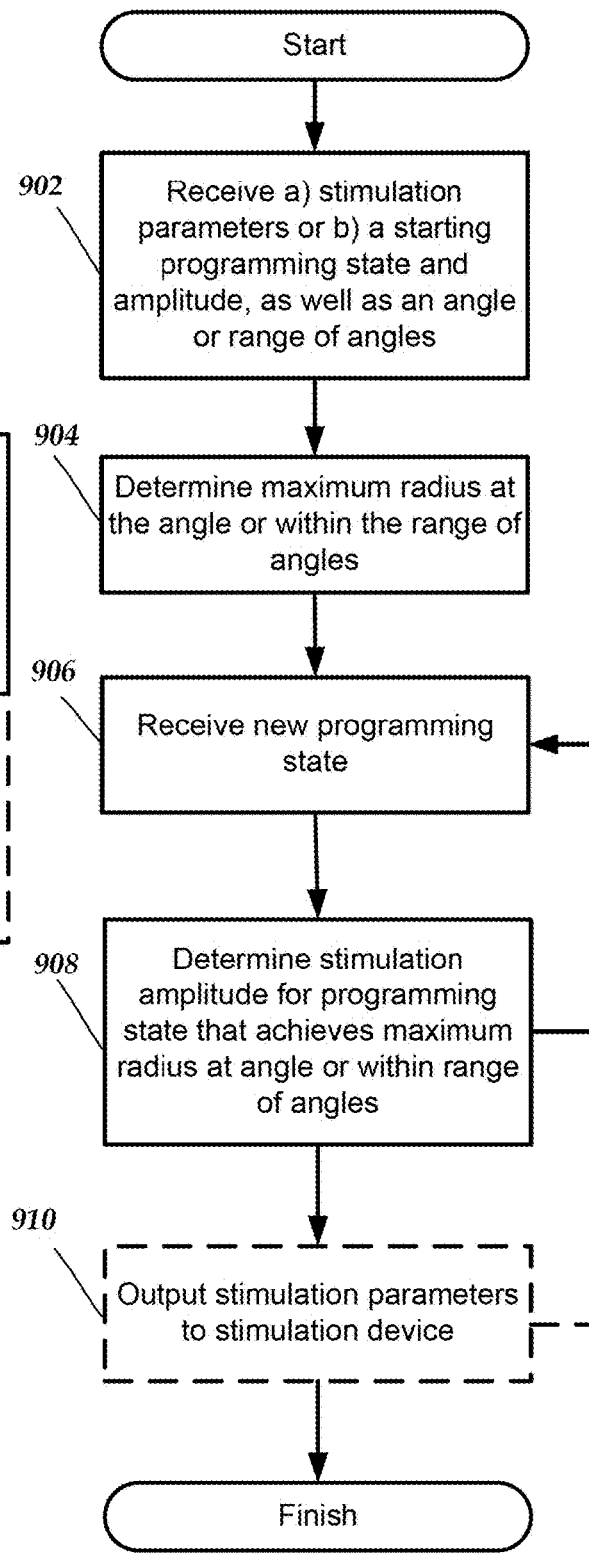
Fig. 8
Fig. 9

SYSTEMS AND METHODS FOR STEERING ELECTRICAL STIMULATION OF PATIENT TISSUE AND DETERMINING STIMULATION PARAMETERS

CROSS-REFERENCE TO RELATED APPLICATIONS

This application claims the benefit under 35 U.S.C. § 119(e) of U.S. Provisional Patent Application Ser. No. 62/397,256, filed Sep. 20, 2016, which is incorporated herein by reference.

FIELD

The invention is directed to the field of electrical stimulation systems. The present invention is also directed to systems and methods for steering electrical stimulation of patient tissue and determining stimulation parameters, as well as methods of making and using systems.

BACKGROUND

Electrical stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MM") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. The electrodes can be formed into rings or segments disposed on a distal portion of the lead. The stimulus current projects from the electrodes. Using segmented electrodes can provide directionality to the stimulus current and permit a clinician to steer the current to a desired direction and stimulation field.

BRIEF SUMMARY

One embodiment is a computer-implemented method for determining a set of stimulation parameters for an electrical stimulation lead, the method including: a) receiving, by a computer processor, a target geometrical parameter describing a stimulation field; b) receiving, by the computer processor, a first programming state; c) determining, by the computer processor, a first stimulation parameter for the first programming state that achieves the target geometrical parameter within at least 10% of the target geometrical parameter; and d) outputting, by the computer processor, a set of stimulation parameters to be received by an electrical stimulation device for delivery of electrical stimulation to a patient via an electrical stimulation lead, wherein the set of stimulation parameters includes the first stimulation parameter and represents the first programming state.

In at least some embodiments, the target geometrical parameter is a target maximum radius, the method further including receiving, by the computer processor, an angle, wherein determining the first stimulation parameter includes determining, by the computer processor, the first stimulation parameter for the first programming state that achieves the target maximum radius at the angle within at least 10% of the target maximum radius.

In at least some embodiments, the target geometrical parameter is a target maximum radius, the method further including receiving, by the computer processor, a range of angles, wherein determining the first stimulation parameter includes determining, by the computer processor, the first stimulation parameter for the first programming state that achieves the target maximum radius within the range of angles within at least 10% of the target maximum radius.

In at least some embodiments, the target geometrical parameter is a target maximum radius, the method further including receiving, by the computer processor, an axial position or range of axial positions, wherein determining the first stimulation parameter includes determining, by the computer processor, the first stimulation parameter for the first programming state that achieves the target maximum radius at the axial position or within the range of axial positions within at least 10% of the target maximum radius.

In at least some embodiments, the method further includes repeating steps b)-d) for at least one additional programming state. In at least some embodiments, determining the first stimulation parameter includes determining, by the computer processor, the first stimulation parameter for the first programming state that achieves the target geometrical parameter within at least 5% of the target geometrical parameter. In at least some embodiments, the target geometrical parameter is a target volume. In at least some embodiments, determining the first stimulation parameter includes determining, by the computer processor, the first stimulation parameter using a look-up table with previously determined first stimulation parameters for a plurality of programming states.

Another embodiment is a computer-implemented method for determining a set of stimulation parameters for an electrical stimulation lead, the method including: a) receiving, by a computer processor, either i) a first set of stimulation parameters or ii) a starting programming state and starting first stimulation parameter; b) determining, by the computer processor and from either i) the first set of stimulation parameters or ii) the starting programming state and starting first stimulation parameter, a target geometrical parameter describing a stimulation field; c) receiving, by the computer processor, a first programming state; d) determining, by the computer processor, a first stimulation parameter for the first programming state that achieves the target geometrical parameter; and e) outputting, by the computer processor, a second set of stimulation parameters to be received by an electrical stimulation device for delivery of electrical stimulation to a patient via an electrical stimulation lead, wherein the set of stimulation parameters includes the first stimulation parameter for the first programming state and represents the first programming state.

In at least some embodiments, the method further includes receiving, by the computer processor, an angle, wherein determining the target geometrical parameter includes determining, by the computer processor, a target maximum radius at the angle. In at least some embodiments, determining the first stimulation parameter includes determining, by the computer processor, the first stimulation parameter for the first programming state that achieves the target maximum radius at the angle within at least 10% of the target maximum radius.

In at least some embodiments, the method further includes receiving, by the computer processor, a range of angles, wherein determining the target geometrical parameter includes determining, by the computer processor, a target maximum radius within the range of angles. In at least some embodiments, determining the first stimulation parameter includes determining, by the computer processor, the first stimulation parameter for the first programming state that achieves the target maximum radius within the range of angles within at least 10% of the target maximum radius.

In at least some embodiments, the method further includes receiving, by the computer processor, an axial position or a range of axial positions, wherein determining the target geometrical parameter includes determining, by the computer processor, the target maximum radius at the angle. In at least some embodiments, determining the first stimulation parameter includes determining, by the computer processor, the first stimulation parameter for the first programming state that achieves the target maximum radius at the axial position or within the axial position within at least 10% of the target maximum radius.

In at least some embodiments, the method further includes repeating steps c)-e) for at least one additional programming state. In at least some embodiments, determining the first stimulation parameter includes determining, by the computer processor, the first stimulation parameter for the first programming state that achieves the target geometrical parameter within at least 5% of the target maximum radius or target volume. In at least some embodiments, the target geometrical parameter is a target volume. In at least some embodiments, determining the first stimulation parameter includes determining, by the computer processor, the first stimulation parameter using a look-up table with previously determined first stimulation parameters for a plurality of programming states.

Yet another embodiment is a system for determining a set of stimulation parameters for an electrical stimulation lead, the system including: a display; and a computer processor coupled to the display and configured and arranged to perform any of the methods describe above.

A further embodiment is a non-transitory computer-readable medium having processor-executable instructions for determining a set of stimulation parameters, the processor-executable instructions when installed onto a device enable the device to perform any of the methods describe above.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 8 is a schematic flowchart of a third embodiment of a method of determining a set of stimulation parameters or steering stimulation with a target maximum radius, according to the invention;

FIG. 9 is a schematic flowchart of a fourth embodiment of a method of determining a set of stimulation parameters or steering stimulation with a target maximum radius, according to the invention;

DETAILED DESCRIPTION

Figure 1:
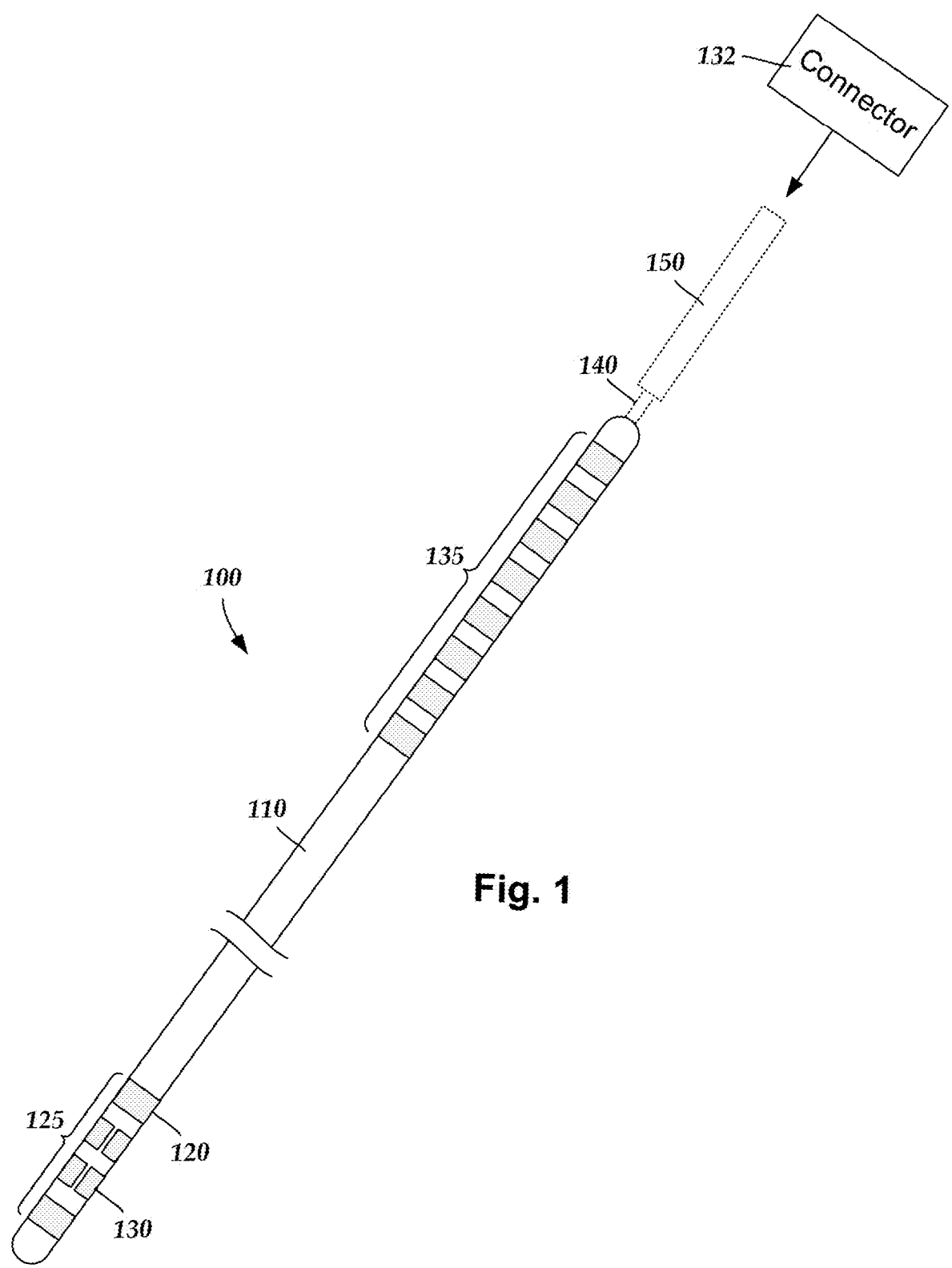
FIG. 1 is a schematic side view of one embodiment of a device for brain stimulation, according to the invention.

The invention is directed to the field of electrical stimulation systems. The present invention is also directed to systems and methods for steering electrical stimulation of patient tissue, as well as methods of making and using systems.

The invention is directed to the field of electrical stimulation systems. The present invention is also directed to systems and methods for visualizing and directing electrical stimulation of neural elements, as well as methods of making and using systems.

A lead for electrical stimulation can include one or more stimulation electrodes. In at least some embodiments, one or more of the stimulation electrodes are provided in the form of segmented electrodes that extend only partially around the circumference of the lead. These segmented electrodes can be provided in sets of electrodes, with each set having electrodes radially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglia stimulation, vagal nerve stimulation, basoreceptor stimulation, or stimulation of other nerves, organs, or tissues.

Suitable implantable electrical stimulation systems include, but are not limited to, at least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead can include both recording electrodes and stimulation electrodes or electrodes can be used for both recording and stimulation.

FIG. 1 illustrates one embodiment of a device 100 for electrical stimulation (for example, brain or spinal cord stimulation). The device includes a lead 110, a plurality of electrodes 125 disposed at least partially about a circumference of the lead 110, a plurality of terminals 135, a connector 132 for connection of the electrodes to a control module, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 132 fits over a proximal end of the lead 110, preferably after removal of the stylet 140. The connector 132 can be part of a control module or can be part of an optional lead extension that is coupled to the control module.

The control module (for example, control module 514 of FIG. 5) can be an implantable pulse generator that can be implanted into a patient's body, for example, below the patient's clavicle area. The control module can have eight stimulation channels which may be independently programmable to control the magnitude of the current stimulus from each channel. In some cases, the control module can have more or fewer than eight stimulation channels (e.g., 4-, 6-, 16-, 32-, or more stimulation channels). The control module can have one, two, three, four, or more connector ports, for receiving the plurality of terminals 135 at the proximal end of the lead 110. Examples of control modules are described in the references cited above.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control module or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes typically do not enable stimulus current to be directed from only a limited angular range around of the lead. Segmented electrodes, however, can be used to direct stimulation energy to a selected angular range around the lead. When segmented electrodes are used in conjunction with an implantable control module that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well. A lead that includes segmented electrodes can be referred to as a directional lead because the segmented electrodes can be used to direct stimulation along a particular direction or range of directions.

The lead 100 includes a lead body 110, one or more optional ring electrodes 120, and a plurality of sets of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Figure 3A:
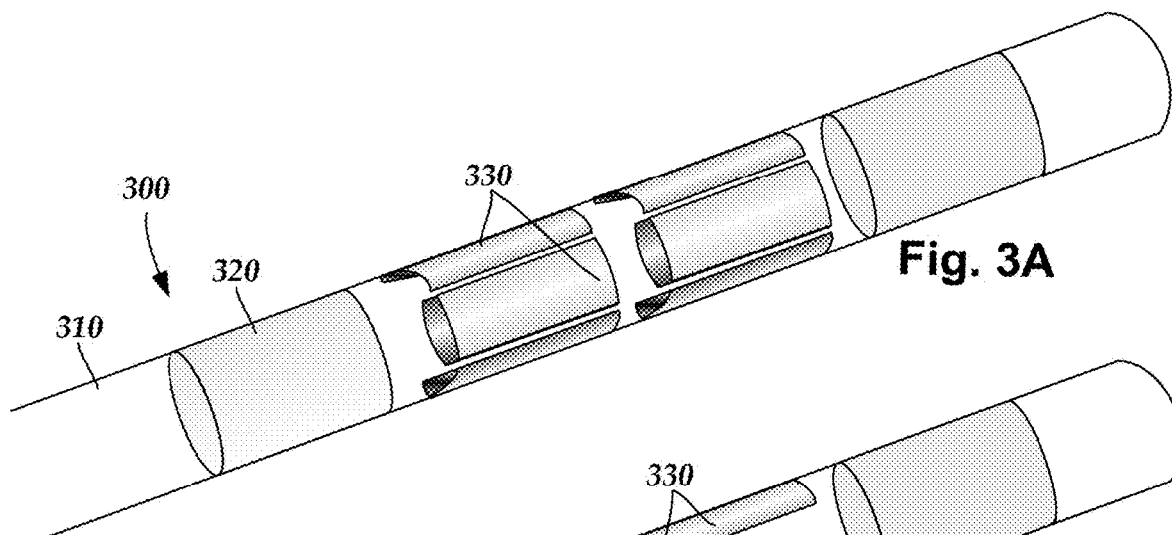
FIG. 3A is a perspective view of an embodiment of a portion of a lead having a plurality of segmented electrodes, according to the invention.
Figure 3B:
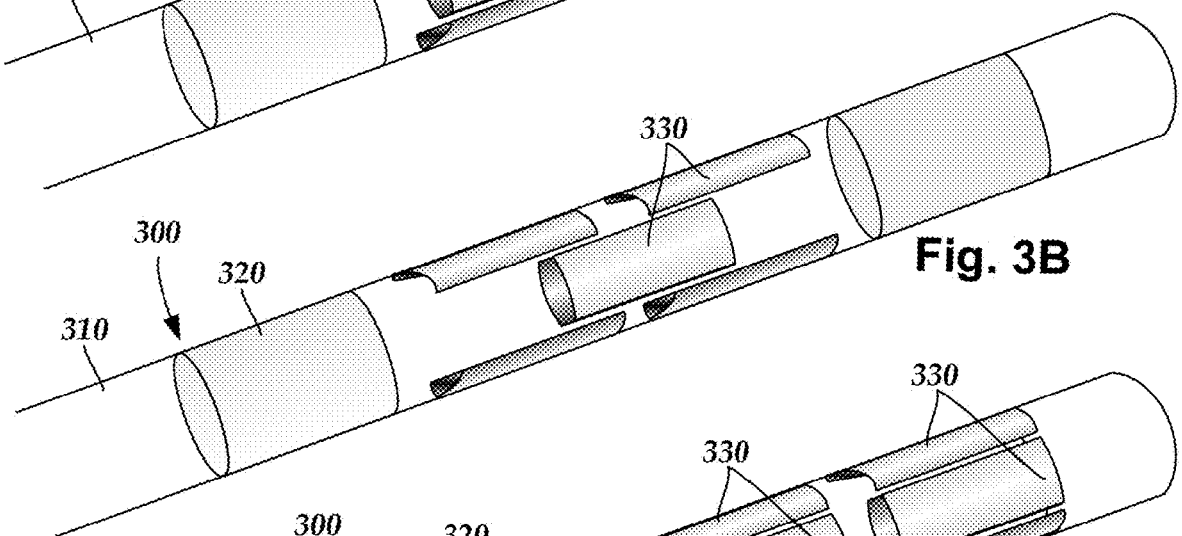
FIG. 3B is a perspective view of a second embodiment of a portion of a lead having a plurality of segmented electrodes, according to the invention.
Figure 3C:
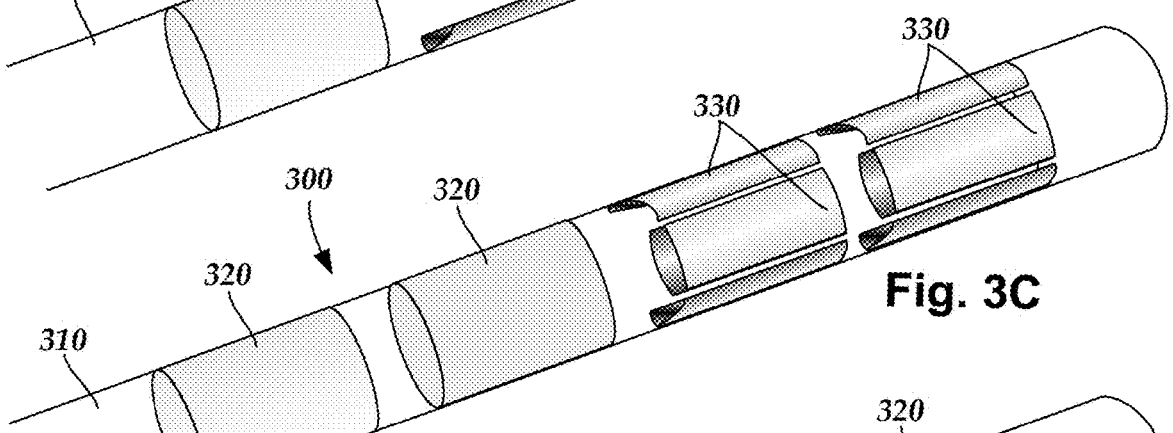
FIG. 3C is a perspective view of a third embodiment of a portion of a lead having a plurality of segmented electrodes, according to the invention.
Figure 3D:
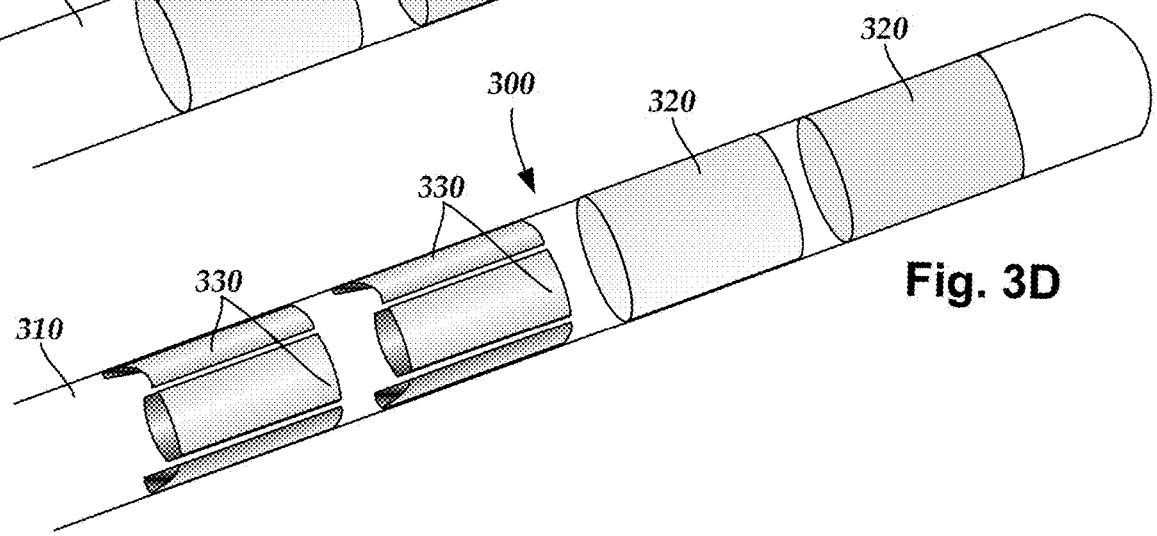
FIG. 3D is a perspective view of a fourth embodiment of a portion of a lead having a plurality of segmented electrodes, according to the invention.
Figure 3E:
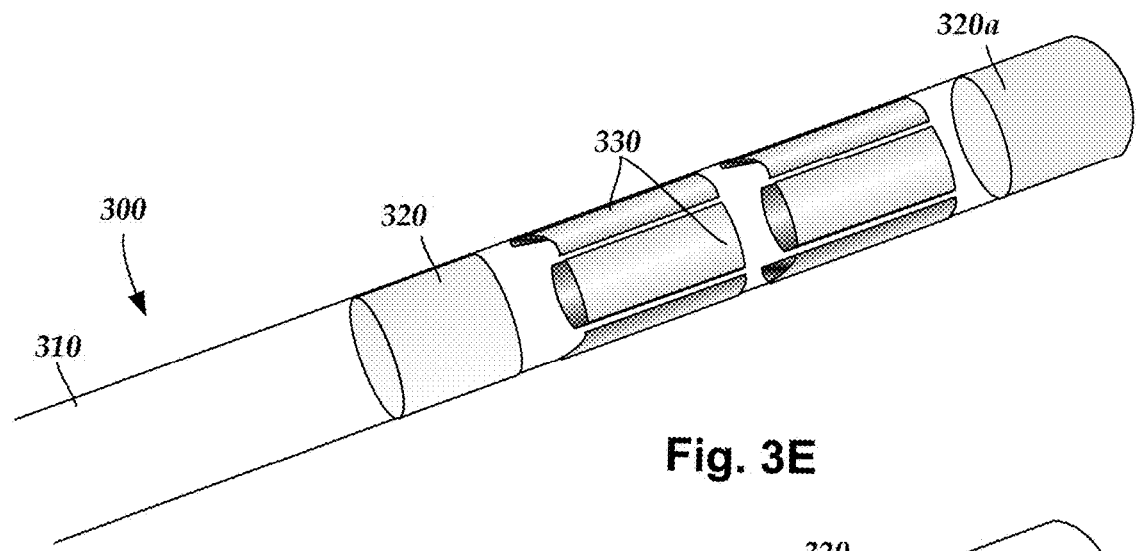
FIG. 3E is a perspective view of a fifth embodiment of a portion of a lead having a plurality of segmented electrodes, according to the invention.
Figure 3F:
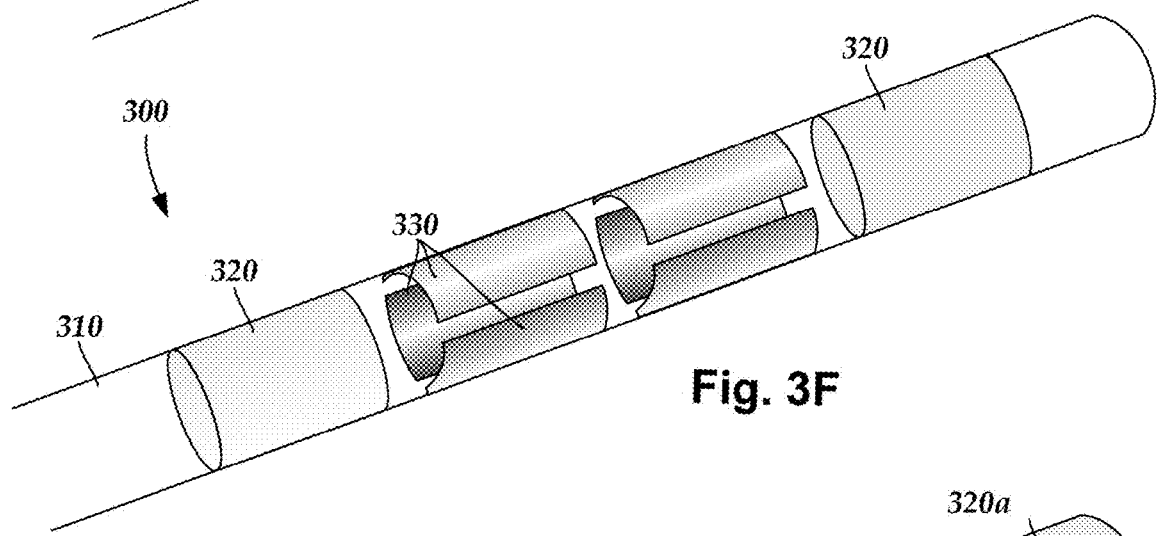
FIG. 3F is a perspective view of a sixth embodiment of a portion of a lead having a plurality of segmented electrodes, according to the invention.

Stimulation electrodes in the form of ring electrodes 120 can be disposed on any part of the lead body 110, usually near a distal end of the lead 100. In FIG. 1, the lead 100 includes two ring electrodes 120. Any number of ring electrodes 120 can be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes can be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120. The distal-most ring electrode 120 may be a tip electrode (see, e.g., tip electrode 320a of FIG. 3E) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array, current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Applications Publication Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. Examples of leads with tip electrodes include at least some of the previously cited references, as well as U.S. Patent Applications Publication Nos. 2014/0296953 and 2014/0343647, all of which are incorporated herein by reference in their entireties.

The lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes 130 may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires that attach to the ring electrodes 120 or segmented electrodes 130 extend along the lead body 110. These conductor wires may extend through the material of the lead 100 or along one or more lumens defined by the lead 100, or both. The conductor wires couple the electrodes 120, 130 to the terminals 135.

When the lead 100 includes both ring electrodes 120 and segmented electrodes 130, the ring electrodes 120 and the segmented electrodes 130 may be arranged in any suitable configuration. For example, when the lead 100 includes two ring electrodes 120 and two sets of segmented electrodes 130, the ring electrodes 120 can flank the two sets of segmented electrodes 130 (see e.g., FIGS. 1, 3A, and 3E-3H—ring electrodes 320 and segmented electrode 330). Alternately, the two sets of ring electrodes 120 can be disposed proximal to the two sets of segmented electrodes 130 (see e.g., FIG. 3C—ring electrodes 320 and segmented electrode 330), or the two sets of ring electrodes 120 can be disposed distal to the two sets of segmented electrodes 130 (see e.g., FIG. 3D—ring electrodes 320 and segmented electrode 330). One of the ring electrodes can be a tip electrode (see, tip electrode 320a of FIGS. 3E and 3G). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful if the physician anticipates that the neural target will be closer to a proximal end of the lead body 110.

Figure 3G:
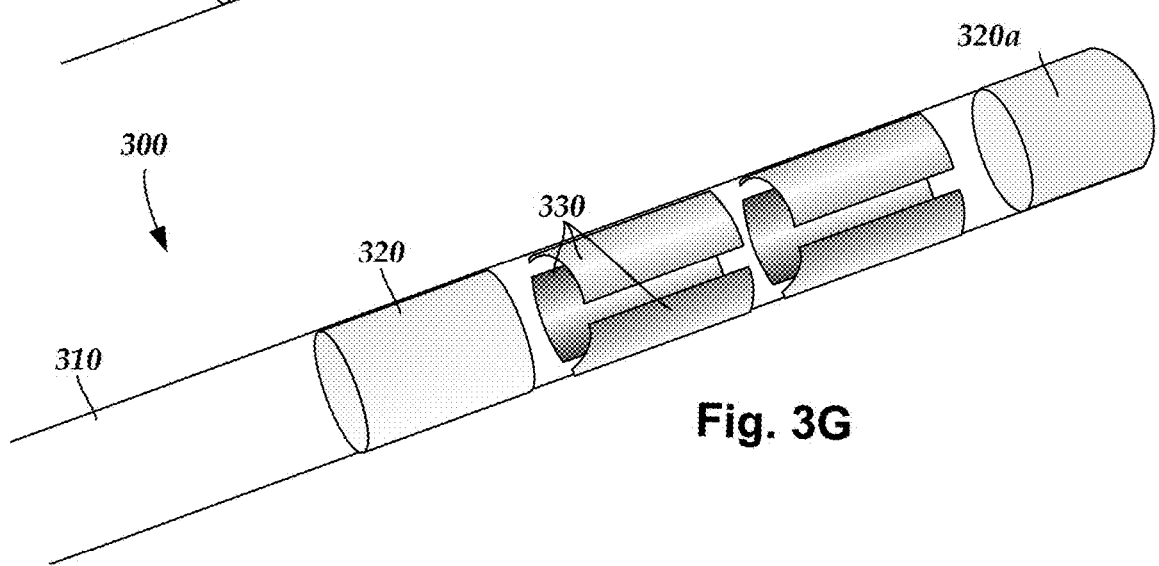
FIG. 3G is a perspective view of a seventh embodiment of a portion of a lead having a plurality of segmented electrodes, according to the invention.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 configuration (FIGS. 3A and 3E—ring electrodes 320 and segmented electrode 330). It may be useful to refer to the electrodes with this shorthand notation. Thus, the embodiment of FIG. 3C may be referred to as a 1-1-4-4 configuration, while the embodiment of FIG. 3D may be referred to as a 4-4-1-1 configuration. The embodiments of FIGS. 3F, 3G, and 3H can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. The 1-3-3-1 electrode configuration of FIGS. 3F, 3G, and 3H has two sets of segmented electrodes, each set containing three electrodes disposed around the circumference of the lead, flanked by two ring electrodes (FIGS. 3F and 3H) or a ring electrode and a tip electrode (FIG. 3G). In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 2:
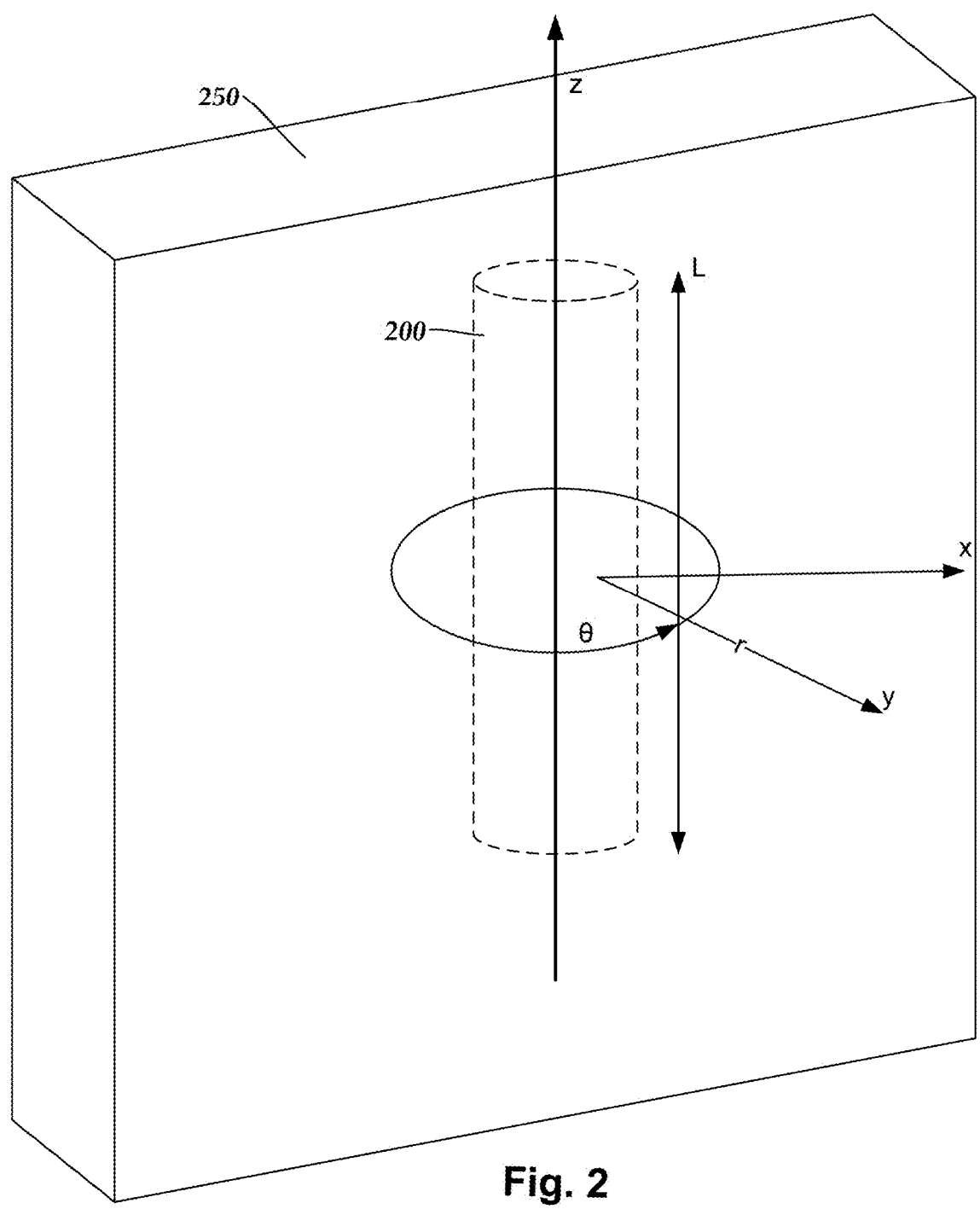
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the stimulation can be shifted at each level along the length L of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes in a set are utilized to allow for true 360° selectivity.

Turning to FIGS. 3A-3H, when the lead 300 includes a plurality of sets of segmented electrodes 330, it may be desirable to form the lead 300 such that corresponding electrodes of different sets of segmented electrodes 330 are radially aligned with one another along the length of the lead 300 (see e.g., the segmented electrodes 330 shown in FIGS. 3A and 3C-3G). Radial alignment between corresponding electrodes of different sets of segmented electrodes 330 along the length of the lead 300 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 300 are radially aligned with one another and do not radially shift in relation to one another during manufacturing of the lead 300.

In other embodiments, individual electrodes in the two sets of segmented electrodes 330 are staggered (see, FIG. 3H) relative to one another along the length of the lead body 310. In some cases, the staggered positioning of corresponding electrodes of different sets of segmented electrodes along the length of the lead 300 may be designed for a specific application.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 250 that contains the electrodes of the lead 200, as illustrated in FIG. 2. One arrangement for directing a stimulation field into a parallelepiped region uses segmented electrodes disposed on opposite sides of a lead.

Figure 3H:
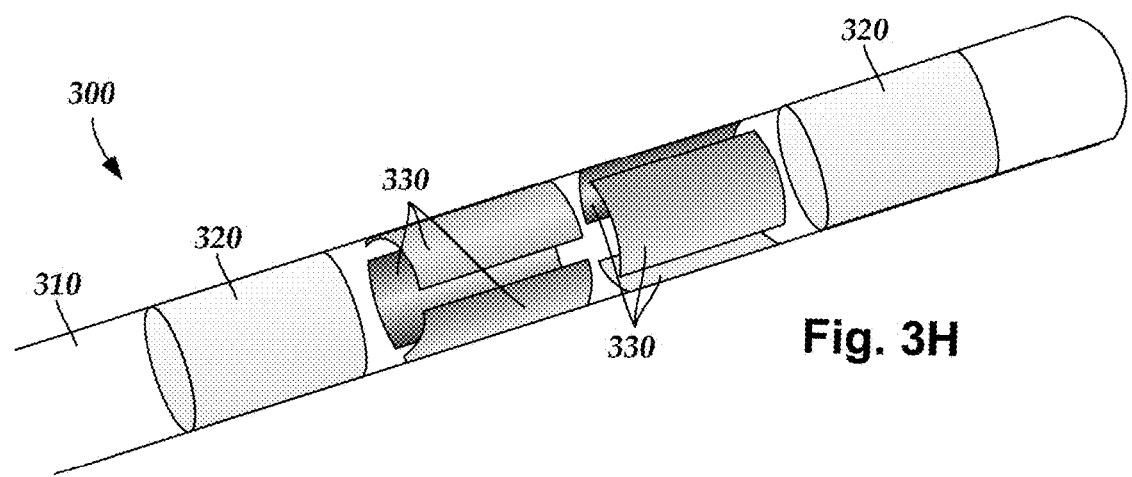
FIG. 3H is a perspective view of an eighth embodiment of a portion of a lead having a plurality of segmented electrodes, according to the invention.

FIGS. 3A-3H illustrate leads 300 with segmented electrodes 330, optional ring electrodes 320 or tip electrodes 320a, and a lead body 310. The sets of segmented electrodes 330 each include either two (FIG. 3B), three (FIGS. 3E-3H), or four (FIGS. 3A, 3C, and 3D) or any other number of segmented electrodes including, for example, three, five, six, or more. The sets of segmented electrodes 330 can be aligned with each other (FIGS. 3A-3G) or staggered (FIG. 3H)

Any other suitable arrangements of segmented electrodes can be used. As an example, arrangements in which segmented electrodes are arranged helically with respect to each other. One embodiment includes a double helix.

Figure 5:
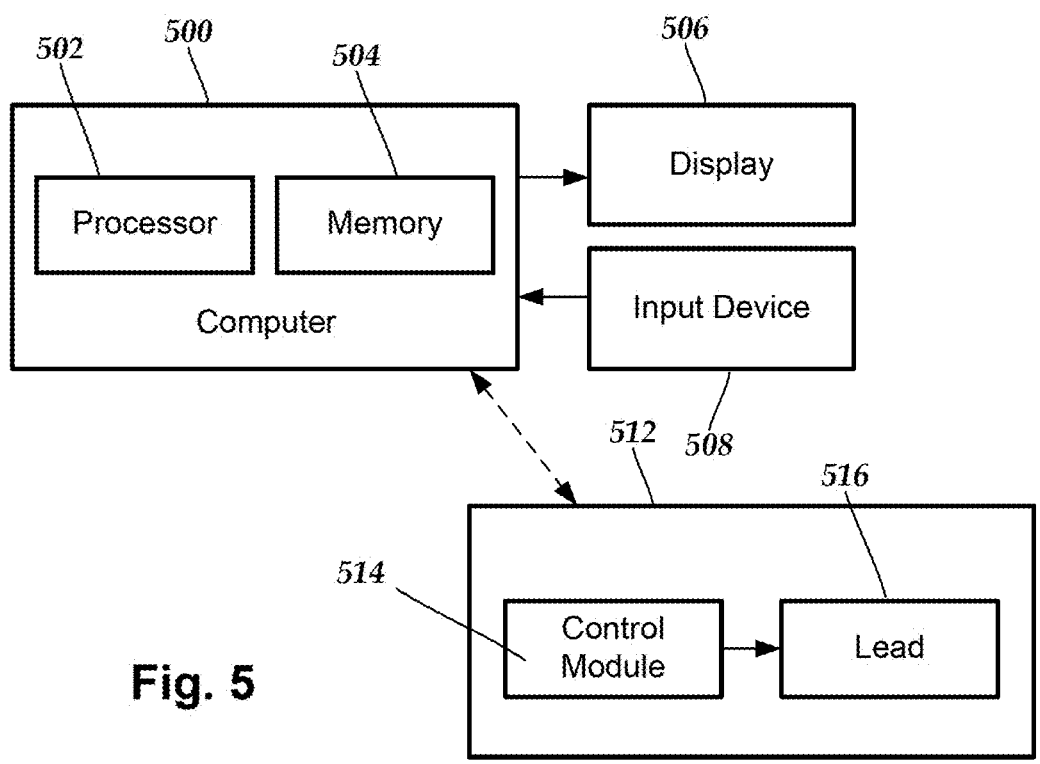
FIG. 5 is a schematic illustration of one embodiment of a system for practicing the invention.

FIG. 5 illustrates one embodiment of a system for practicing the invention. The system can include a computer 500 or any other similar device that includes a processor 502 and a memory 504, a display 506, an input device 508, and, optionally, the electrical stimulation system 512.

The computer 500 can be a laptop computer, desktop computer, tablet, mobile device, smartphone or other devices that can run applications or programs, or any other suitable device for processing information and for presenting a user interface (such as the user interfaces of FIGS. 5A, 5B, 6A-6C, 9, and 5). The computer can be, for example, a clinician programmer, patient programmer, or remote programmer for the electrical stimulation system 512. The computer 500 can be local to the user or can include components that are non-local to the user including one or both of the processor 502 or memory 504 (or portions thereof). For example, in some embodiments, the user may operate a terminal that is connected to a non-local computer. In other embodiments, the memory can be non-local to the user.

The computer 500 can utilize any suitable processor 502 including one or more hardware processors that may be local to the user or non-local to the user or other components of the computer. The processor 502 is configured to execute instructions provided to the processor, as described below.

Any suitable memory 504 can be used for the computer 502. The memory 504 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 506 can be any suitable display device, such as a monitor, screen, display, or the like, and can include a printer. The input device 508 can be, for example, a keyboard, mouse, touch screen, track ball, joystick, voice recognition system, or any combination thereof, or the like and can be used by the user to interact with a user interface or clinical effects map.

The electrical stimulation system 512 can include, for example, a control module 514 (for example, an implantable pulse generator) and a lead 516 (for example, the lead illustrated in FIG. 1.) The electrical stimulation system 512 may communicate with the computer 500 through a wired or wireless connection or, alternatively or additionally, a user can provide information between the electrical stimulation system 512 and the computer 500 using a computer-readable medium or by some other mechanism. In some embodiments, the computer 500 may include part of the electrical stimulation system.

In at least some instances, a treating physician may wish to tailor the stimulation parameters (such as which one or more of the stimulating electrode contacts to use, the stimulation pulse amplitude (such as current or voltage amplitude depending on the stimulator being used,) the stimulation pulse width, the stimulation frequency, or the like or any combination thereof) for a particular patient to improve the effectiveness of the therapy. Electrical stimulation systems can provide an interface that facilitates parameter selections. Examples of such systems and interfaces can be found in, for example, U.S. patent application Ser. Nos. 12/454,330; 12/454,312; 12/454,340; 12/454,343; and 12/454,314 and U.S. Patent Application Publication No. 2014/0277284, all of which are incorporated herein by reference in their entireties.

Stimulation region visualization systems and methods can be used to predict or estimate a region of stimulation for a given set of stimulation parameters. In at least some embodiments, the systems and methods further permit a user to modify stimulation parameters and visually observe how such modifications can change the predicted or estimated stimulation region. Such algorithms and systems may provide greater ease of use and flexibility and may enable or enhance specific targeting of stimulation therapy. The terms "stimulation field map" (SFM) and "volume of activation" (VOA) are often used to designate an estimated region of tissue that will be stimulated for a particular set of stimulation parameters. Any suitable method for determining the VOA/SFM can be used including those described in, for example, U.S. Pat. Nos. 8,326,433; 8,675,945; 8,831,731; 8,849,632; and 8,958,615; U.S. Patent Application Publications Nos. 2009/0287272; 2009/0287273; 2012/0314924; 2013/0116744; 2014/0122379; and 2015/0066111; and U.S. Provisional Patent Application Ser. No. 62/030,655, all of which are incorporated herein by reference.

Figure 4:
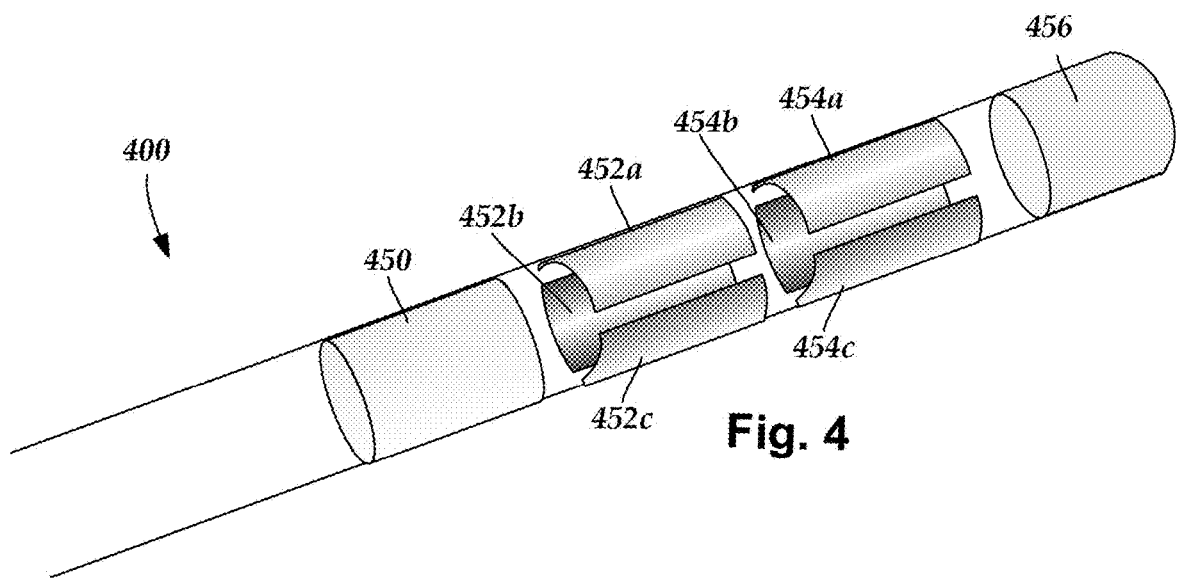
FIG. 4 is a perspective view of a ninth embodiment of a portion of a lead having a plurality of segmented electrodes, according to the invention.

For purposes of illustration of the methods and systems described below, one embodiment of a distal end of a lead 400 is presented in FIG. 4. The lead 400 includes a ring electrode 450, a first set of three segmented electrodes 452a, 452b, 452c, a second set of three segmented electrodes 454a, 454b, 454c, and a tip electrode 456. A number of state variables can be used to describe the electrical stimulation field. First, a "position" variable can be used to estimate or represent the central axial position of the field relative to the longitudinal axis of the lead. For example, if the stimulation is provided solely by ring electrode 450, then the position of the field is centered on ring electrode 450. However, combinations of electrodes can also be used. For example, if the stimulation is provided with 50% of the amplitude on ring electrode 450 and 50% of the amplitude on segmented electrode 452a, then the position of the field can be described as between electrodes 450, 452a (although it will be recognized that the field also extends in both axial directions from this position.)

Another state variable is "rotation" which represents the radial direction of the field. In the case of stimulation provided solely by ring electrode 450, the rotation variable is arbitrary because the stimulation is provided in all directions. On the other hand, if the stimulation is provided by segmented electrode 452a, the rotation can be described as directed outward from segmented electrode 452a. Again, combinations of electrodes can be used so that the rotation may be described as between electrodes 452a, 452b if 50% of the stimulation amplitude is provided to both electrodes.

Yet another state variable is "spread" which relates to the spread of the field around the circumference of the lead. In the case of stimulation provided solely by ring electrode 450, the spread variable is at a maximum because the stimulation is provided in all directions. On the other hand, if the stimulation is provided by segmented electrode 452a, the spread variable is at its minimum because the field is generated by only one segmented electrode 452a. Again, combinations of electrodes can be used so that the spread may be described as larger when 50% of the stimulation amplitude is provided on both electrodes 452a, 452b.

The stimulation (e.g., stimulation current) can be steered by changing these state variables. For example, the stimulation can be moved up or down the longitudinal axis of the lead by changing the position variable. As an example, the stimulation can be initially provided 100% through electrode 450. The stimulation can then be steered distally by directing a portion of the stimulation to the electrodes 452a, 452b, 452c. For example, in a first step, 90% of the stimulation remains on electrode 450 and 10% is divided equally among electrodes 452a, 452b, 452c. The second step can have 80% on electrodes 450 and 20% divided equally among electrodes 452a, 452b, 452c. This can continue until there is no stimulation on electrode 450 and 100% of the stimulation is divided among electrodes 452a, 452b, 452c. The process can proceed to incrementally transfer stimulation from electrodes 452a, 452b, 452c to electrodes 454a, 454b, 454c. Similarly, the stimulation then be incrementally transferred from electrodes 454a, 454b, 454c to electrode 456. The stimulation can also be rotated. For example, stimulation from electrode 452a and be rotated to electrode 452 b. The stimulation field can also be spread. For example, stimulation field from electrode 452a can be spread so that the stimulation is from both electrodes 452a, 452b. That stimulation field can then be contracted so that the stimulation is only from electrode 452b.

It has been found, however, that the SFMs determined using these incremental steering steps can vary substantially in maximum radius (e.g., the maximum extent of the SFM measured orthogonal to the lead) despite having the same stimulation amplitude. In at least some instances, the maximum radius of the SFM can vary by 20%, 30%, 40% or more as the stimulation is steered along the lead with constant stimulation amplitude.

In at least some instances, it is desirable to steer stimulation along or around a lead and maintain a constant or nearly constant (e.g., within 1, 2, 3, 4, 5, 10, or 15%) maximum radius of the stimulation field. This can be accomplished by changing one or more stimulation parameters, such as stimulation amplitude, pulse width, or the like, to maintain the stimulation within the specified constraint, such as a specified maximum radius. Methods and systems for performing such steering are provided below.

In general, the methods and systems described herein include selection of one or more target geometrical parameters, such as a target maximum radius or a target volume, and maintenance of that target geometrical parameter with changes in programming state by determining one or more stimulation parameters that maintain the target geometrical parameter for the new programming state. In the examples below, target maximum radius and target volume are used as examples of the target geometrical parameter. The methods and systems described below can be used with any other suitable geometrical parameter including, but not limited to, a target minimum radius or other target radius, a target diameter, a target axial length (at the lead or at any distance from the lead such as at the edge of the encapsulation layer), a target cross-sectional area at any plane or plane sections relative to the lead (including planes orthogonal to, including, parallel to, or at any angle relative to the longitudinal axis of the lead) or the like. In addition, the methods and systems described below can be used with more than one target geometrical parameter including, for example, multiple target radii at different angles distributed around the lead.

In at least some embodiments of the methods and systems described herein, the maintenance of the target geometrical parameter can be performed to maintain the target geometrical parameter at the same value. In other embodiments, the maintenance of the target geometrical parameter can be performed to maintain the target geometrical parameter within 1, 2, 3, 4, 5, 10%, or 15% of the original or target value. Unless otherwise indicated, the maintenance of the target geometrical parameter is performed to maintain the target geometrical parameter within 10% of the target value. In some embodiments, the percentage deviation from the original value that is allowed is fixed and not user-defined. In other embodiments, the percentage deviation from the original value that is allowed can be user-defined or user-modified from an initial value.

Instead of maintaining the target geometrical parameter within a particular percentage, in some embodiments, the one or more stimulation parameters are selected so that the stimulation field does not exceed (e.g., is less than or equal) the target geometrical parameter or at a minimum meets (e.g. is greater than or equal) the target geometrical parameter. In yet other embodiments, for example, when the stimulation parameter can only be changed in discreet steps (for example, stimulation amplitude may only be variable in steps of 0.1 mA), the target geometrical parameter is maintained using the largest (or smallest) value of the stimulation parameter for which the resulting stimulation field does not exceed (e.g., is less than or equal) the target geometrical parameter or at a minimum meets (e.g. is greater than or equal) the target geometrical parameter.

It will be recognized that the stimulation fields described herein are not necessarily the actual stimulation field generated upon application of a set of stimulation parameters. Instead, the stimulation field, and associated geometrical parameter, can be estimates or approximations calculated based on models, such as those discussed above for determining SFMs or VOAs.

In addition, in the examples of systems and methods described below, stimulation amplitude is altered to maintain the target geometrical parameter, but it will be recognized that other stimulation parameters can be used instead of stimulation amplitude including, but not limited to, pulse width, stimulation frequency, or the like. Moreover, in some embodiments, two or more stimulation parameters can be altered to maintain the target geometrical parameter.

In at least some embodiments of the systems and methods described herein, a table of maximum radii (or other geometrical parameter) can be determined for multiple programming states that are defined by multiple programming state variables, such as position, rotation, spread, pulse width, amplitude, and the like. Each of the programming states is defined using two or more of these programming state variables. The maximum radius can then be determined for each of these programming states. For example, a look-up table of maximum radii can be defined for a set of programming states using, as programming state variables, pulse width, spread, rotation, position, and amplitude. As one example, such a table can be generated for a set of programming states obtained using 44 different pulse widths, 11 different spreads, 12 different rotations, 31 different positions, and 16 different amplitudes. The number of possible values for each programming state variable can be varied from this example, as well as the selection of which programming state variable to use. Such a look-up table can then be used in the methods described below.

Figure 6:
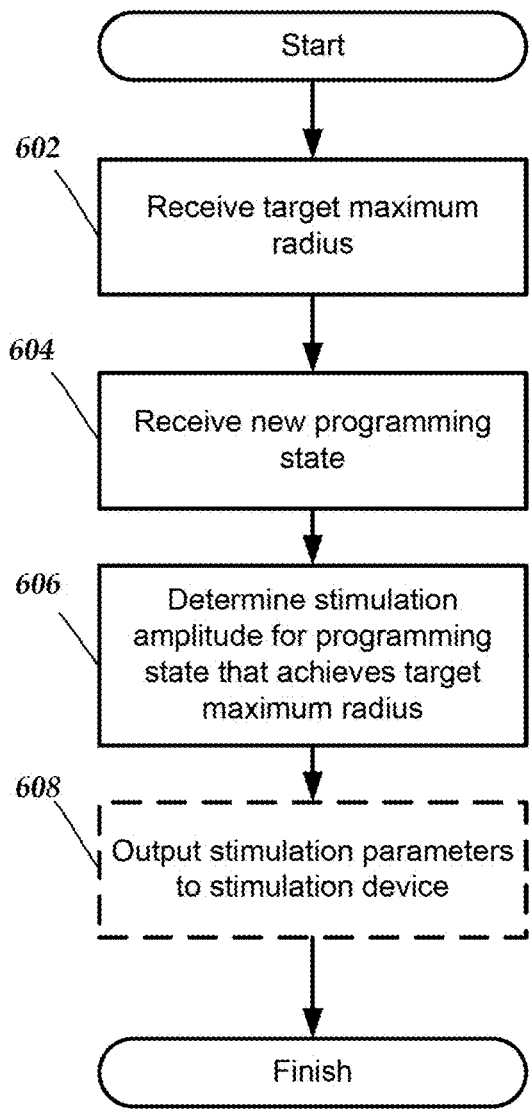
FIG. 6 is a schematic flowchart of one embodiment of a method of determining a set of stimulation parameters or steering stimulation with a target maximum radius, according to the invention.

FIG. 6 illustrates one example of a method of maintaining a selected maximum radius during a change in programming state. In this method, the target maximum radius is received and the stimulation amplitude is then adjusted to obtain the target maximum radius at different programming states.

In step 602, a target maximum radius is received from a clinician, user, or other source. In step 604, a desired programming state is received.

In step 606, the stimulation amplitude is determined that produces the target maximum radius for the desired programming state. In at least some embodiments, the stimulation amplitude (or other stimulation parameter) can be determined from a look-up table, such as the one described above, which provides maximum radii for multiple programming states. If the target maximum radius or programming state are not provided in the look-up table, then interpolation between entries can be used to obtain a stimulation amplitude that corresponds to the target maximum radius and desired programming state. Any suitable interpolation technique can be used including linear or non-linear interpolation techniques.

Alternatively or additionally, a model of the neural region near the lead can be created, such as the models used for the calculation of SFMs or VOAs as discussed in the references cited above. The model can determine, for each volume element in the region, the threshold stimulation current needed to activate a neural element at that volume element. In at least some embodiments, the stimulation amplitude can be determined to be the minimum threshold stimulation current for the volume elements at the target maximum radius.

In optional step 608, stimulation parameters based on the stimulation amplitude and programming state are output to a stimulation device, for example, the control module of FIG. 5, that can produce stimulation signals for delivery to the patient via the lead electrodes. The stimulation parameters can be associated with the programming state including, for example, the pulse width and selection of electrodes corresponding to the spread, rotation, and position state variables, as well as the division of the stimulation amplitude between electrodes where there are more than one anode or cathode. For example, the processor performing the method of FIG. 6 can initiate a signal directed to the stimulation device in order to convey the stimulation parameters to the stimulation device. The stimulation device can receive the stimulation parameters and can then operate a stimulation program to deliver electrical stimulation to the patient using the stimulation parameters.

In at least some embodiments, after performing step 606 or step 608, the process can return to step 604 to receive a new programming state. Steps 606 and, optionally, step 608 can be then be performed based on the new programming state. This process can be repeated as many times as desired for any number of programming states.

Figure 7:
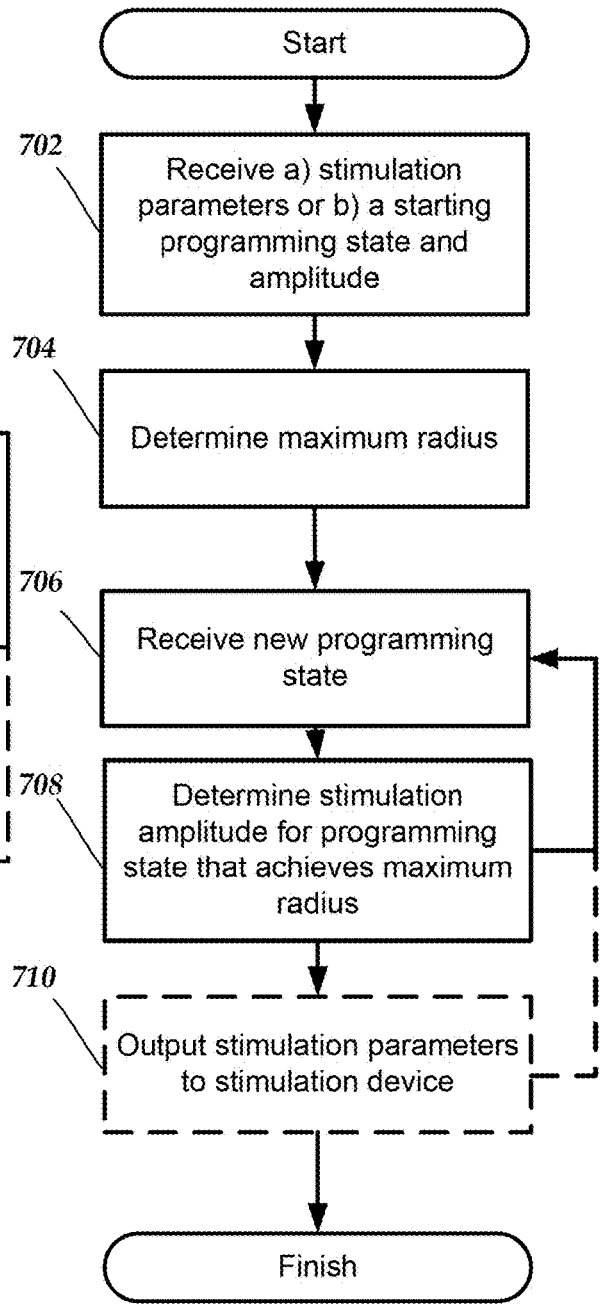
FIG. 7 is a schematic flowchart of another embodiment of a method of determining a set of stimulation parameters or steering stimulation with a target maximum radius, according to the invention.

FIG. 7 illustrates one example of a method of maintaining a selected maximum radius during a change in programming state. In this method, either a set of steering parameters or a starting programming state and starting stimulation amplitude is received. A maximum radius is determined from the initial information and then stimulation amplitude is adjusted to obtain the maximum radius at different programming states.

In step 702, either a) stimulation parameters (including a starting stimulation amplitude) or b) a starting programming state and starting stimulation amplitude is received from a clinician, user, or other source.

In step 704, the maximum radius is determined based on the information received in step 702. In some embodiments, the maximum radius is determined from a look-up table, such as the look-up table described above. In other embodiments, the maximum radius can be determined using the SFM/VOA calculation methods described above. In yet other embodiments, the maximum radius can be determined from a model of the neural region near the lead, such as the models used for the calculation of SFMs or VOAs as discussed in the references cited above. The model can determine, for each volume element in the region, the threshold stimulation current needed to activate a neural element at that volume element. In at least some embodiments, the maximum radius can correspond to the largest radius at which the starting stimulation amplitude is equal to the threshold stimulation current for one of the volume elements at that radius.

In step 706, a desired programming state is received. In step 708, the stimulation amplitude (or other stimulation parameter) is determined that produces the maximum radius for the desired programming state. In at least some embodiments, the stimulation amplitude can be determined from a look-up table, such as the one described above, which provides maximum radii for multiple programming states. If the maximum radius or programming state are not provided in the look-up table, then interpolation between entries can be used to obtain a stimulation amplitude that corresponds to the maximum radius and desired programming state. Any suitable interpolation technique can be used including linear or non-linear interpolation techniques.

Alternatively or additionally, a model of the neural region near the lead can be created, such as the models used for the calculation of SFMs or VOAs as discussed in the references above. The model can determine, for each volume element in the region, the threshold stimulation current needed to activate a neural element at that volume element. In at least some embodiments, the stimulation amplitude can be determined to be the minimum threshold stimulation current for the volume elements at the maximum radius.

In optional step 710, stimulation parameters based on the stimulation amplitude and programming state are output to a stimulation device, for example, the control module of FIG. 5, that can produce stimulation signals for delivery to the patient via the lead electrodes. The stimulation parameters can be associated with the programming state including, for example, the pulse width and selection of electrodes corresponding to the spread, rotation, and position state variables, as well as the division of the stimulation amplitude between electrodes where there are more than one anode or cathode. For example, the processor performing the method of FIG. 7 can initiate a signal directed to the stimulation device in order to convey the stimulation parameters to the stimulation device. The stimulation device can receive the stimulation parameters and can then operate a stimulation program to deliver electrical stimulation to the patient using the stimulation parameters.

In at least some embodiments, after performing step 708 or step 710, the process can return to step 706 to receive a new programming state. Steps 708 and, optionally, step 710 can be then be performed based on the new programming state. This process can be repeated as many times as desired for any number of programming states.

In the methods described with respect to FIGS. 6 and 7, there is no spatial limit on where the maximum radius can reside. The directional leads illustrated in, for example, 3A-3F and 4, can be used to generate stimulation that is not symmetric around the longitudinal axis of the lead, but rather can have directionality with respect to the longitudinal axis of the lead. For example, providing stimulation current using electrode 452a and not electrodes 452b, 452c will extend the stimulation from electrode 452a which much less stimulation near electrodes 425b, 452c.

FIGS. 8 and 9 illustrated embodiments of methods of maintaining a selected maximum radius at an angle or range of angles during a change in programming state. The steps of FIGS. 8 and 9 are the same as those in FIGS. 6 and 7, respectively, except as noted below.

In step 802, in addition to receiving the target maximum radius, an angle or range of angles where the target maximum radius is to reside is also received. In step 806, the stimulation amplitude (or other stimulation parameter) that achieves the target maximum radius at the specified angle or within the specified range of angles is determined.

Similarly, in step 902, an angle or range of angles is received in addition to the other information. In step 904, the maximum radius is determined at that angle or within that range of angles. In step 908, the stimulation amplitude that achieves the maximum radius at the specified angle or within the specified range of angles is determined.

The methods can be further modified. For example, in steps 804 and 906, in addition to receiving a new programming state, a new angle or range of angles can be received. The stimulation amplitude (or other stimulation parameter) determined in steps 806 and 908 will achieve the maximum radius for the new angle or within the new range of angles. This modification to the methods can be used to maintain a constant radius at the stimulation is rotated around a lead.

Yet another modification can include specifying a particular axial position or range of axial positions along the lead where the target maximum radius is to reside instead of, or in addition to, the angle or range of angles in the methods of FIGS. 8 and 9 or the modified methods described in the preceding paragraph.

Instead of maintaining a constant maximum radius, a constant volume can be maintained. The volume for a particular state can be determined by calculation of a SFM or VOA and then determining the volume of that SFM or VOA. In at least some embodiments, a table of maximum volumes can be determined for multiple states that are defined by multiple state variables, such as position, rotation, spread, pulse width, amplitude, and the like. Each of the states is defined using two or more of these state variables. The maximum volume can then be determined for each of these states. For example, a look-up table of maximum volumes can be defined for a set of states using, as state variables, pulse width, spread, rotation, position, and amplitude. As one example, such a table can be generated for a set of states obtained using 44 different pulse widths, 11 different spreads, 12 different rotations, 31 different positions, and 16 different amplitudes. The number of possible values for each state variable can be varied from this example, as well as the selection of which state variable to use. Such a look-up table can then be used in the methods described below.

Figure 10:
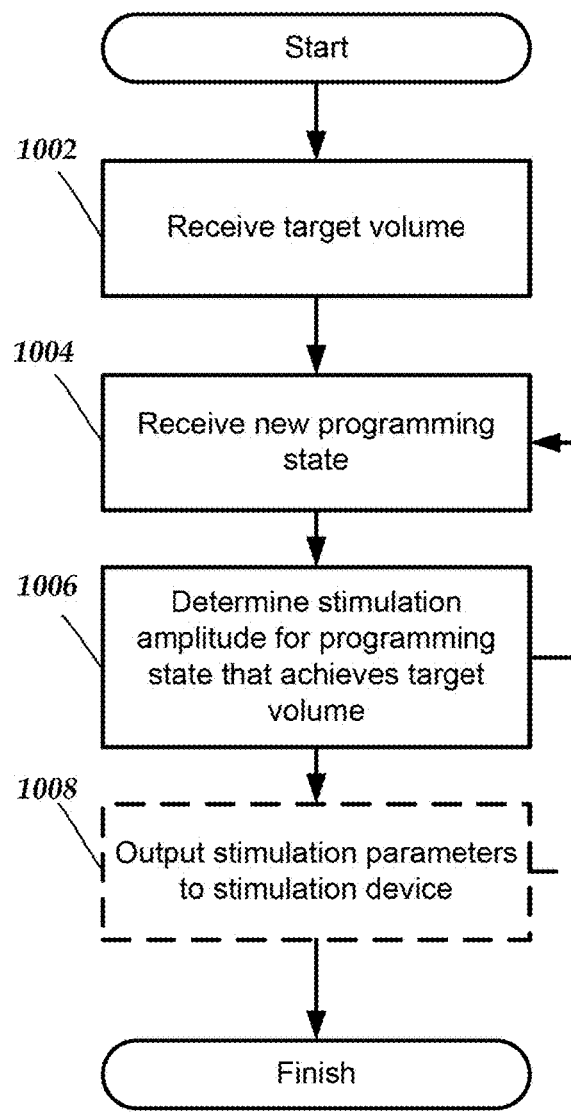
FIG. 10 is a schematic flowchart of one embodiment of a method of determining a set of stimulation parameters or steering stimulation with a target volume, according to the invention.

FIG. 10 illustrates one example of a method of maintaining a selected volume during a change in programming state. In this method, the target volume is received and the stimulation amplitude is adjusted to obtain the target volume at different programming states.

In step 1002, a target volume is received from a clinician, user, or other source. In step 1004, a desired programming state is received.

In step 1006, the stimulation amplitude (or other stimulation parameter) is determined that produces the target volume for the desired programming state. In at least some embodiments, the stimulation amplitude can be determined from a look-up table, such as the one described above, which provides maximum radii for multiple programming states. If the target volume or programming state are not provided in the look-up table, then interpolation between entries can be used to obtain a stimulation amplitude that corresponds to the target volume and desired programming state. Any suitable interpolation technique can be used including linear or non-linear interpolation techniques.

Alternatively or additionally, a model of the neural region near the lead can be created, such as the models used for the calculation of SFMs or VOAs as discussed in the references above. The model can determine, for each volume element in the region, the threshold stimulation current needed to activate a neural element at that volume element. In at least some embodiments, a stimulation field can be created by sequentially increasing a current value and adding volume elements with a threshold stimulation current equal to the current value until the target volume is reached. Alternatively, a stimulation field can be created by sequentially decreasing a current value and subtracting volume elements with a threshold stimulation current greater than the current value until the target volume is reached. In either case, the final current value at which the target volume is reached is the stimulation current.

In optional step 1008, stimulation parameters based on the stimulation amplitude and programming state are output to a stimulation device, for example, the control module of FIG. 5, that can produce stimulation signals for delivery to the patient view the lead electrodes. The stimulation parameters can be associated with the programming state including, for example, the pulse width and selection of electrodes corresponding to the spread, rotation, and position state variables, as well as the division of the stimulation amplitude between electrodes where there are more than one anode or cathode. For example, the processor performing the method of FIG. 10 can initiate a signal directed to the stimulation device in order to convey the stimulation parameters to the stimulation device. The stimulation device can receive the stimulation parameters and can then operate a stimulation program to deliver electrical stimulation to the patient using the stimulation parameters.

In at least some embodiments, after performing step 1006 or step 1008, the process can return to step 1004 to receive a new programming state. Steps 1006 and, optionally, step 1008 can be then be performed based on the new programming state. This process can be repeated as many times as desired for any number of programming states.

Figure 11:
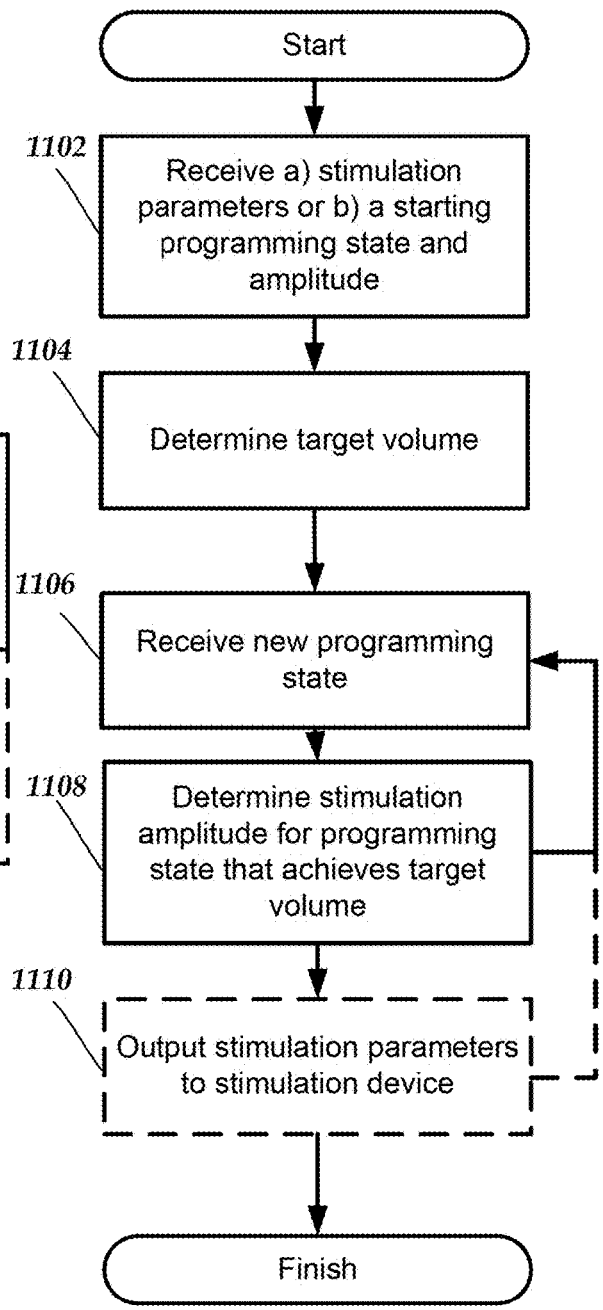
FIG. 11 is a schematic flowchart of another embodiment of a method of determining a set of stimulation parameters or steering stimulation with a target volume, according to the invention.

FIG. 11 illustrates one example of a method of maintaining a selected target volume during a change in programming state. In this method, either a set of steering parameters or a starting programming state and starting stimulation amplitude is received. A target volume is determined from the initial information and then stimulation amplitude is adjusted to obtain the target volume at different programming states.

In step 1102, either a) stimulation parameters (including a starting stimulation amplitude) or b) a starting programming state and starting stimulation amplitude is received from a clinician, user, or other source. In step 1104, the target volume is determined based on the information provided in step 1102. In some embodiments, the target volume is determined from a look-up table, such as the look-up table described above. In other embodiments, the target volume can be determined using the SFM/VOA calculation methods described above.

In step 1106, a desired programming state is received. In step 1108, the stimulation amplitude (or other stimulation parameter) is determined that produces the target volume for the desired programming state. In at least some embodiments, the stimulation amplitude can be determined from a look-up table, such as the one described above, which provides maximum radii for multiple programming states. If the target volume or programming state are not provided in the look-up table, then interpolation between entries can be used to obtain a stimulation amplitude that corresponds to the target volume and desired programming state. Any suitable interpolation technique can be used including linear or non-linear interpolation techniques.

Alternatively or additionally, a model of the neural region near the lead can be created, such as the models used for the calculation of SFMs or VOAs as discussed in the references above. The model can determine, for each volume element in the region, the threshold stimulation current needed to activate a neural element at that volume element. In at least some embodiments, a stimulation field can be created by sequentially increasing a current value and adding volume elements with a threshold stimulation current equal to the current value until the target volume is reached. Alternatively, a stimulation field can be created by sequentially decreasing a current value and subtracting volume elements with a threshold stimulation current greater than the current value until the target volume is reached. In either case, the final current value at which the target volume is reached is the stimulation current.

In optional step 1110, stimulation parameters based on the stimulation amplitude and programming state are output to a stimulation device, for example, the control module of FIG. 5, that can produce stimulation signals for delivery to the patient view the lead electrodes. The stimulation parameters can be associated with the programming state including, for example, the pulse width and selection of electrodes corresponding to the spread, rotation, and position state variables, as well as the division of the stimulation amplitude between electrodes where there are more than one anode or cathode. For example, the processor performing the method of FIG. 11 can initiate a signal directed to the stimulation device in order to convey the stimulation parameters to the stimulation device. The stimulation device can receive the stimulation parameters and can then operate a stimulation program to deliver electrical stimulation to the patient using the stimulation parameters.

In at least some embodiments, after performing step 1108 or step 1110, the process can return to step 1106 to receive a new programming state. Steps 1108 and, optionally, step 1110 can be then be performed based on the new programming state. This process can be repeated as many times as desired for any number of programming states.

Similar to the methods illustrated in FIGS. 8 and 9, the methods illustrated in FIGS. 10 and 11 can be modified so to maintain a target volume within a specified range of angles or within a specified axial range or both.

In other embodiments, the methods described herein may be modified to allow the user to select whether to maintain the maximum radius or maintain the target volume (or maintain another geometrical parameter). For example, the user may be permitted to specify whether to maintain the maximum radius or maintain the target volume at the start of the process. In other embodiments, the user may be permitted to specify whether to maintain the maximum radius or maintain the target volume each time a new programming state is received.

In yet other embodiments, the process may incorporate rules (which may or may not be user-modifiable or user-selectable) to determine whether to maintain the maximum radius or maintain the target volume (or other geometrical parameter). For example, the rules may specify that when decreasing a state variable, the maximum radius is maintained and when increasing that state variable, the target volume is maintained (or vice versa).

As one example, reducing the spread state variable often decreases the stimulation amplitude needed to maintain constant radius, while increasing the spread state variable at constant radius increases the volume of stimulation. Accordingly, one example of a rule is that when decreasing spread the maximum radius is maintained and when increasing spread the target volume is maintained (or vice versa).

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage

What is claimed as new and desired to be protected by Letters Patent of the United States is:

1. A method for determining a set of electrical stimulation parameters for an electrical stimulation lead and delivering electrical stimulation, the method comprising:
    a) receiving, by a computer processor, a target geometrical parameter describing an electrical stimulation field, wherein the target geometrical parameter is a target maximum radius;
    b) receiving, by the computer processor, one of the following: an angle, a range of angles, an axial position, or a range of axial positions;
    c) receiving, by the computer processor, a first programming state;
    d) determining, by the computer processor, a first electrical stimulation parameter for the first programming state that achieves the target geometrical parameter within at least 10% of the target geometrical parameter at the angle when the angle is received in step b), within the range of angles when the range of angles is received in step b), at the axial position when the axial position is received in step b) or within the range of axial positions when the range of axial positions is received in step b);
    e) outputting, by the computer processor, a set of electrical stimulation parameters to be received by an electrical stimulation device for delivery of electrical stimulation to a patient via an electrical stimulation lead, wherein the set of electrical stimulation parameters comprises the first electrical stimulation parameter and represents the first programming state; and
    f) delivering the electrical stimulation to the patient using the set of electrical stimulation parameters.

2. The method of claim 1, wherein the angle is received in step b).

3. The method of claim 1, wherein the range of angles is received in step b).

4. The method of claim 1, wherein the axial position or the range of axial positions is received in step b).

5. The method of claim 1, further comprising repeating steps c)-e) for at least one additional programming state.

6. A method for determining a set of electrical stimulation parameters for an electrical stimulation lead and delivering electrical stimulation, the method comprising:
    a) receiving, by a computer processor, a target geometrical parameter describing an electrical stimulation field;
    b) receiving, by the computer processor, a first programming state;
    c) determining, by the computer processor, a first electrical stimulation parameter for the first programming state that achieves the target geometrical parameter within at least 10% of the target geometrical parameter, wherein determining the first electrical stimulation parameter comprises determining, by the computer processor, the first electrical stimulation parameter using a look-up table with previously determined first electrical stimulation parameters for a plurality of programming states;
    d) outputting, by the computer processor, a set of electrical stimulation parameters to be received by an electrical stimulation device for delivery of electrical stimulation to a patient via an electrical stimulation lead, wherein the set of electrical stimulation parameters comprises the first electrical stimulation parameter and represents the first programming state; and
    e) delivering the electrical stimulation to the patient using the set of electrical stimulation parameters.

7. The method of claim 6, wherein the target geometrical parameter is a target volume.

8. A method for determining a set of electrical stimulation parameters for an electrical stimulation lead, the method comprising:
    a) receiving, by a computer processor, either i) a first set of electrical stimulation parameters or ii) a starting programming state and starting first electrical stimulation parameter;
    b) the computer processor, one of the following: an angle, a range of angles, an axial position, or a range of axial positions;
    c) determining, by the computer processor and from either i) the first set of electrical stimulation parameters or ii) the starting programming state and starting first electrical stimulation parameter, a target geometrical parameter describing an electrical stimulation field, wherein the target geometrical parameter is a target maximum radius;
    d) receiving, by the computer processor, a first programming state;
    e) determining, by the computer processor, a first electrical stimulation parameter for the first programming state that achieves the target geometrical parameter within at least 10% of the target geometrical parameter at the angle when the angle is received in step b), within the range of angles when the range of angles is received in step b), at the axial position when the axial position is received in step b) or within the range of axial positions when the range of axial positions is received in step b);
    f) outputting, by the computer processor, a second set of electrical stimulation parameters to be received by an electrical stimulation device for delivery of electrical stimulation to a patient via an electrical stimulation lead, wherein the set of electrical stimulation parameters comprises the first electrical stimulation parameter for the first programming state and represents the first programming state; and
    g) delivering the electrical stimulation to the patient using the set of electrical stimulation parameters.

9. The method of claim 8, wherein the angle is received in step b), wherein determining the target geometrical parameter comprises determining, by the computer processor, the target maximum radius at the angle.

10. The of claim 8, wherein the range of angles is received in step b), wherein determining the target geometrical parameter comprises determining, by the computer processor, the target maximum radius within the range of angles.

11. The method of claim 8, wherein the axial position or a range of axial positions is received in step b), wherein determining the target geometrical parameter comprises determining, by the computer processor, the target maximum radius at the axial position or within the range of axial positions.

12. The method of claim 8, further comprising repeating steps d)-f) for at least one additional programming state.

13. The computer-implemented method of claim 8, wherein determining the first electrical stimulation parameter comprises determining, by the computer processor, the first electrical stimulation parameter using a look-up table with previously determined first electrical stimulation parameters for a plurality of programming states.

14. A system for determining a set of electrical stimulation parameters for an electrical stimulation lead and delivering electrical stimulation, the system comprising:
 a display;
 a computer processor coupled to the display; and
 an electrical stimulation device comprising an electrical stimulation lead and in communication with the computer processor;
 wherein the electrical stimulation system is configured and arranged to perform the method of claim 1.

15. A system for determining a set of electrical stimulation parameters for an electrical stimulation lead and delivering electrical stimulation, the system comprising:
 a display;
 a computer processor coupled to the display; and
 an electrical stimulation device comprising an electrical stimulation lead and in communication with the computer processor;
 wherein the electrical stimulation system is configured and arranged to perform the method of claim 8.

16. A non-transitory computer-readable medium having processor-executable instructions for determining a set of electrical stimulation parameters and delivering electrical stimulation, the processor-executable instructions when installed onto a device enable the device to perform the method of claim 1.

17. A system for determining a set of electrical stimulation parameters for an electrical stimulation lead and delivering electrical stimulation, the system comprising:
 a display;
 a computer processor coupled to the display; and
 an electrical stimulation device comprising an electrical stimulation lead and in communication with the computer processor;
 wherein the electrical stimulation system is configured and arranged to perform the method of claim 6.

18. A non-transitory computer-readable medium having processor-executable instructions for determining a set of electrical stimulation parameters and delivering electrical stimulation, the processor-executable instructions when installed onto a device enable the device to perform the method of claim 6.

19. A non-transitory computer-readable medium having processor-executable instructions for determining a set of electrical stimulation parameters and delivering electrical stimulation, the processor-executable instructions when installed onto a device enable the device to perform the method of claim 8.

* * * * *